US009802993B2

(12) United States Patent
Tabuchi et al.

(10) Patent No.: US 9,802,993 B2
(45) Date of Patent: Oct. 31, 2017

(54) METHOD FOR PRODUCING A CELL FOR PROTEIN PRODUCTION BY TREATING A CELL OVEREXPRESSING A TAURINE TRANSPORTER WITH METHOTREXATE

(75) Inventors: Hisahiro Tabuchi, Tokyo (JP); Tomoya Sugiyama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/733,815

(22) PCT Filed: Oct. 14, 2008

(86) PCT No.: PCT/JP2008/068589
§ 371 (c)(1),
(2), (4) Date: Mar. 22, 2010

(87) PCT Pub. No.: WO2009/051109
PCT Pub. Date: Apr. 23, 2009

(65) Prior Publication Data
US 2011/0003334 A1    Jan. 6, 2011

(30) Foreign Application Priority Data
Oct. 15, 2007    (JP) .................................. 2007-267384

(51) Int. Cl.
*C12P 21/00*    (2006.01)
*C12P 21/08*    (2006.01)
*C07K 14/47*    (2006.01)
*C07K 16/30*    (2006.01)

(52) U.S. Cl.
CPC ............ *C07K 14/47* (2013.01); *C07K 16/303* (2013.01); *C12N 2500/33* (2013.01); *C12N 2501/06* (2013.01); *C12N 2510/02* (2013.01)

(58) Field of Classification Search
CPC ......... C12P 21/00; C12P 21/005; C12P 21/02; C12N 15/00; C12N 15/09; C12N 9/003; C12N 9/88; C12Y 105/01003; C12Y 401/01029
USPC ...................... 435/69.1, 70.1, 70.3, 191, 232
See application file for complete search history.

(56) References Cited

U.S. PATENT DOCUMENTS

| | | | |
|---|---|---|---|
| 5,658,786 A | 8/1997 | Smith et al. | |
| 6,184,007 B1 | 2/2001 | Dusch et al. | |
| 6,225,115 B1 | 5/2001 | Smith et al. | |
| 6,251,613 B1 | 6/2001 | Kishimoto et al. | |
| 6,316,238 B1 | 11/2001 | Nakamura et al. | |
| 6,812,339 B1 | 11/2004 | Venter et al. | |
| 7,413,536 B1 | 8/2008 | Dower et al. | |
| 7,919,086 B2 | 4/2011 | Nakano et al. | |
| 8,697,397 B2 * | 4/2014 | Tabuchi et al. | 435/70.3 |
| 2003/0165495 A1 | 9/2003 | Carulli et al. | |
| 2004/0014218 A1 * | 1/2004 | Lee | C07K 14/4747 435/455 |
| 2005/0221466 A1 | 10/2005 | Liao et al. | |
| 2005/0265983 A1 | 12/2005 | Melamed et al. | |
| 2006/0014937 A1 | 1/2006 | Kang et al. | |
| 2006/0068445 A1 * | 3/2006 | Furusako | C07K 14/70596 435/7.1 |
| 2007/0162995 A1 | 7/2007 | Good et al. | |
| 2007/0166362 A1 | 7/2007 | Sakuma et al. | |
| 2007/0190599 A1 | 8/2007 | Nakano et al. | |
| 2009/0191591 A1 * | 7/2009 | Tabuchi et al. | 435/69.6 |
| 2009/0221442 A1 | 9/2009 | Dower et al. | |
| 2010/0167346 A1 | 7/2010 | Tabuchi et al. | |
| 2010/0233759 A1 * | 9/2010 | Tabuchi et al. | 435/69.1 |
| 2010/0248359 A1 | 9/2010 | Nakano et al. | |
| 2011/0014654 A1 | 1/2011 | Tabuchi et al. | |
| 2012/0045795 A1 | 2/2012 | Tabuchi et al. | |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO-92/04381 A1 | 3/1992 |
| WO | WO-97/27485 A1 | 7/1997 |
| WO | WO-01/20331 A1 | 3/2001 |
| WO | WO-02/092768 A2 | 11/2002 |
| WO | WO-03/039485 A2 | 5/2003 |

(Continued)

OTHER PUBLICATIONS

Han et al., "Taurine 6", Springer, New York 2006, pp. 59-67.*
Wirth et al., Gene 73:419-426, 1988.*
Lee et al., Biotechnol. Bioengineer. 82:872-876, 2003.*
Ifandi et al., Biotechnol. Prog. 21:671-677, 2005.*
Tang et al., J. Neurosci. 17:6947-6951, 1997.*
De La Rosa et al., Comp. Biochem. Physiol. 81B:565-571, 1985.*
Herman et al., Inflamm. Res. 54:273-280, 2005.*
Pilbrough et al., PLoS One 4:e8432, 2009, 11 pages.*
Galivan, J., Cancer Res. 39:735-743, 1979.*
International Search Report mailed Nov. 11, 2008, in PCT/JP2008/068589, 6 pages.
Christensen et al., "High expression of the taurine transporter TauT in primary cilic of NIH3T3 fibroblasts," Cell Biology International, 2005, 29:347-351.

(Continued)

*Primary Examiner* — David J Steadman
(74) *Attorney, Agent, or Firm* — Foley & Lardner LLP

(57) ABSTRACT

The present invention provides a cell capable of high-yield production of polypeptides and a method for producing the same. The present invention relates to a method for producing a cell capable of high-yield production of a desired polypeptide, wherein a strongly taurine transporter-expressing cell into which DNA encoding the desired polypeptide has been introduced is cultured in the presence of a high concentration of methotrexate and a cell capable of high-yield production of the desired polypeptide is selected from among surviving cells.

8 Claims, 6 Drawing Sheets

(56) References Cited

FOREIGN PATENT DOCUMENTS

| | | |
|---|---|---|
| WO | WO-2005/076015 A1 | 8/2005 |
| WO | WO-2006/006693 A1 | 1/2006 |
| WO | WO-2006/119115 A2 | 11/2006 |
| WO | WO-2007/056507 A1 | 5/2007 |
| WO | WO 2007/119774 A1 | 10/2007 |
| WO | WO 2008/114673 A1 | 9/2008 |
| WO | WO-2009/020144 A1 | 2/2009 |
| WO | WO-2009/051109 A1 | 4/2009 |
| WO | WO-2009/054433 A1 | 4/2009 |

OTHER PUBLICATIONS

Hwang et al., "Expression and purification of recombinant human angiopoietin-2 produced in Chinese hamster ovary cells," Protein Expression and Purification, 2005, 39:175-183.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Liu et al., "Cloning and expression of a cDNA encoding the transporter taurine and β-alanine in mouse brain," Proc. Natl. Acad. Sci. USA, Dec. 1992, 89:12145-12149.

Miyasaka et al., "Characterization of Human Taurine Transporter Expressed in Insect Cells Using a Recombinant Baculovirus," Protein Expression and Purification, 2001, 23:389-397.

Smith et al., "Cloning and Expression of a High Affinity Taurine Transporter from Rat Brain," Molecular Pharmacology, 1992, 42:563-569.

Tappaz et al., "Characterization of the cDNA Coding for Rat Brain Cysteine Sulfinate Decarboxylase: Brain and Liver Enzymes are Identical Proteins Encoded by Two Distince mRNAs," Journal of Neurochemistry, 1999, 73:903-912.

Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.

Final Office Action dated Dec. 17, 2010 in U.S. Appl. No. 12/226,195.

Final Office Action dated Mar. 2, 2012 in U.S. Appl. No. 12/734,283.

Notice of Allowance dated Dec. 20, 2012 in U.S. Appl. No. 12/733,052.

Office Action dated May 18, 2010 in U.S. Appl. No. 12/226,195.
Office Action dated Aug. 3, 2011 in U.S. Appl. No. 12/734,283.
Office Action dated Sep. 21, 2012 in U.S. Appl. No. 13/368,945.

Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.

Office Action dated Feb. 27, 2013 in U.S. Appl. No. 13/138,909.
Final Office Action dated May 24, 2013 in U.S. Appl. No. 13/368,945.

Tanner et al., "The complete amino acid sequence of the human erythrocyte membrane anion-transport protein deduced from the cDNA sequence," Biochem. J., 1988, 256:703-712.

Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(5),2496-2505.

Han et al., "Regulation of TauT by cisplatin in LLC-PK1 renal cells," Pediatr. Nephrol., 2005, 20:1067-1072.

Ishiguro et al., "CO2 permeability and bicarbonate transport in microperfused interlobular ducts isolated from guinea-pig pancreas," Journal of Physiology, 2000, 528.2:305-315.

Mount et al., "The SLC26 gene family of multifunctional anion exchangers," Pflugers Arch.—Eur. J. Physiol., 2004, 447:710-721.

Pushkin et al., "SLC4 base (HCO-3, CO-23) transporters: classification, function, structure, genetic diseases, and knockout models," Am. J. Physiol. Renal Physiol., 2006, 290:F580-F599.

U.S. Appl. No. 13/368,945, filed Feb. 8, 2012, Tabuchi et al.

Alper, Seth L., "Molecular physiology of SLC4 anion exchangers," Exp. Physiol., 2006, 91:153-161.

Arden et al., "Life and death in mammalian cell culture: strategies for apoptosis inhibition," Trends in Biotechnology, Apr. 2004, 22(4):174-180.

Bell et al., "Genetic Engineering of Hybridoma Glutamine Metabolism," Enzyme and Microbial Technology, 1995, 17(2):98-106.

Butler, Michael, "Animal cell cultures: recent achievements and perspectives in the production of biopharmaceuticals," Appl. Microbiol. Biotechnol., 2005, 68:283-291.

Chambard et al., "Sugar transport by mammalian members of the SLC26 superfamily of anion-bicarbonate exchangers," J. Physiol., 2003, 550:667-677.

Christie et al., "The Adaptation of BHK Cells to a Non-Ammoniagenic Glutamate-Based Culture Medium," Biotechnology and Bioengineering, Aug. 5, 1999, 64(3):298-309.

Database DDBJ/EMBL/GenBank [online], Accession No. NM_000342, uploaded Sep. 25, 2007, Keskanokwong et al., Definition: Homo sapiens solute carrier family 4, anion exchanger, member 1 (erythrocyte membrane protein band 3, Diego blood group) (SLC4A1), mRNA, retrieved Nov. 11, 2008, 12 pages.

Database EMBL [Online] Jul. 23, 1992, XP002593029, retrieved from EBI accession No. EMBL:M95495, 3 pages.

Database Uniprot [Online] Jan. 10, 2006, XP002593032, retrieved from EBI accession No. UNIPROT:Q2VRP7, 1 page.

Database UniProt [Online] Jul. 1, 1993, XP002593028, retrieved from EBI accession No. UNIPROT:Q00589, 2 pages.

Database UniProt [Online] Jun. 1, 2001, "RecName: Full=Cysteine sulfinic acid decarboxylase; EC=<A>; AltName: Full=Cysteine-sulfinate decarboxylase; AltName: Full=Sulfinoalanine decarboxylase;" XP002597738 retrieved from EBI accession No. UNIPROT:Q9DBE0 Database accession No. Q9DBEO, 2 pages.

Database Uniprot [Online] Mar. 15, 2005, XP002593030, retrieved from EBI accession No. UNIPROT:Q5F431, 1 page.

Database Uniprot [Online] Oct. 1, 2000, XP002593031, retrieved from EBI accession No. UNIPROT:Q9MZ34, 2 pages.

De la Cruz Edmonds et al., "Development of Transfection and High-Producer Screening Protocols for the CHOK1SV Cell System," Molecular Biology, Oct. 1, 2006, 34(2):179-190.

Dusch et al., "Expression of the Corynebacterium glutamicum panD Gene Encoding L-Aspartate-alpha-Decarboxylase Leads to Pantothenate Overproduction in Escherichia coli," Applied and Environmental Microbiology, Apr. 1999, 65(4):1530-1539.

Final Office Action dated Mar. 1, 2012 in U.S. Appl. No. 12/733,052.

Fu et al., "Direct interaction and cooperative role of tumor suppressor p16 with band 3 (AE1)," FEBS Letters, 2005, 579(10):2105-2110.

Ganapathy et al., "Expression and Regulation of the Taurine Transporter in Cultured Cell Lines of Human Origin," Advances in Experimental Medicine and Biology, 1994, 359:51-57, XP009123192.

GenBank Accession No. AEQ38544, Oct. 2011, 2 pages.
GenBank Accession No. EGW01898, Aug. 2011, 2 pages.

Good et al., "Engineering nitrogen use efficiency with alanine aminotransferase," Canadian Journal of Botany, Mar. 1, 2007, 85(3):252-262.

Griffith, Owen W., "Cysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Ito et al., "Expression of taurine transporter is regulated through the TonE (tonicity-responsive element)/TonEBP (TonE-binding protein) pathway and contributes to cytoprotection in HepG2 cells," Biochem. J., 2004, 382:177-182.

(56) References Cited

OTHER PUBLICATIONS

Jhiang et al., "Cloning of the human taurine transporter and characterization of taurine uptake in thyroid cells," FEBS Letters, Mar. 1993, 318(2):139-144.
Kalwy et al., "Toward More Efficient Protein Expression," Molecular Biology, Oct. 2006, 34(2):151-156.
Kennell et al,. "Principles and Practices of Nucleic Acid Hybridization," Prog. Nucleic Acid Res. Mol. Biol., 1971, 11:259-270.
Kim et al., "Response of recombinant Chinese hamster ovary cells to hyperosmotic pressure: effect of Bcl-2 overexpression," Journal of Biotechnology, 2002, 95:237-248.
Kondo et al., "Modulation of apoptosis by endogenous Bcl-xL expression in MKN-45 human gastric cancer cells," Oncogene, 1998, 17:2585-2591.
Lux et al., "Cloning and characterization of band 3, the human erythrocyte anion-exchange protein (AE1)," Proc. Natl. Acad. Sci. USA, Dec. 1989, 86:9089-9093.
Morgan et al., "Interactions of transmembrane carbonic anhydrase, CAIX, with bicarbonate transporters," Am. J. Physiol. Cell Physiol., Aug. 2007, 293(2):C738-C748.
Ngo et al., "Computational Complexity, Protein Structure Prediction, and the Levinthal Paradox," The Protein Folding Problem and Tertiary Structure Prediction, Merz et al. (Eds.), 1994, 433 and 492-495.
Office Action dated May 12, 2011 in U.S. Appl. No. 12/733,052.
Office Action dated Aug. 9, 2011 in U.S. Appl. No. 12/450,161.
Porter et al., "Non-steady-state kinetics of brain glutamate decarboxylase resulting from interconversion of the apo- and holoenzyme," Biochimica et Biophysica Acta, 1988, 874:235-244.
Ramamoorthy et al., "Functional characterization and chromosomal localization of a cloned taurine transporter from human placenta," Biochem. J., 1994, 300:893-900.

Reymond et al., "Molecular cloning and sequence analysis of the cDNA encoding rat liver cysteine sulfinate decarboxylase (CSD)," Biochimica et Biophysica Acta, 1996, 1307:152-156.
Rudinger, J., "Characteristics of the amino acids as components of a peptide hormone sequence," Peptide Hormones, Parsons (Ed.), 1976, 1-7.
Shen et al., "Expression of Anion Exchanger 1 Sequestrates p16 in the Cytoplasm in Gastric and Colonic Adenocarcinoma," Neoplasia, Oct. 2007, 9(10):812-819.
Tinland et al., "Agrobacterium tumefaciens transfers single-stranded transferred DNA (T-DNA) into the plant cell nucleus," Proc. Natl. Acad. Sci. USA, Aug. 1994, 91:8000-8004.
Trill et al., "Production of monoclonal antibodies in COS and CHO cells," Current Opinion in Biotechnology, 1995, 6:553-560.
Uchida et al., "Molecular cloning of the cDNA for an MDCK cell Na+- and Cl-dependent taurine transporter that is regulated by hypertonicity," PNAS, Sep. 1992, 89(17):8230-8234.
Voss et al., "Regulation of the expression and subcellular localization of the taurine transporter TauT in mouse NIH3T3 fibroblasts," Eur. J. Biochem., Dec. 2004, 271(23-24):4646-4658.
Wu et al., "Overexpression of Anion Exchanger 2 in Human Hepatocellular Carcinoma," Chinese Journal of Physiology, 2006, 49(4):192-198.
Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.
Zhang et al., "Metabolic characteristics of recombinant Chinese hamster ovary cells expressing glutamine synthetase in presence and absence of glutamine," Cytotechnology, 2006, 51(1):21-28.
Han et al., "Mechanisms of regulation of taurine transporter activity," Taurine 6, Edited by Oja and Saransaari, 2006, 79-90.

* cited by examiner

```
         10        20        30        40        50        60        70        80        90       100       110       120
atggctgactcaaaaaccactcaatgccctggatggggaccctgtggctgtggagtccttactccgggatgtgtttgggattgttgtagatgaggccattcggaaagggaccagtgcctcg
 M  A  D  S  K  P  L  N  A  L  D  G  D  P  V  A  V  E  S  L  L  R  D  V  P  G  I  V  V  D  E  A  I  R  K  G  T  S  A  S
        130       140       150       160       170       180       190       200       210       220       230       240
gagaaggtttgtgaatggaaggagcctgaagagctcaagcatctgctggatttggagctgcagagccagggcgagtctcaagagcagattctagagcgctgccgggctgtgattcactac
 E  K  V  C  E  W  K  E  P  E  E  L  K  H  L  L  D  L  E  L  Q  S  Q  G  E  S  Q  E  Q  I  L  E  R  C  R  A  V  I  H  Y
        250       260       270       280       290       300       310       320       330       340       350       360
agtgtcaagactggtcaccccggttcttcaaccagctcttctcagggttagaccccatgtctggctgggcgcatcatcacagaaagcctcaacaccagccagtacacatatgagatt
 S  V  K  T  G  H  P  R  F  F  N  Q  L  F  S  G  L  D  P  H  A  L  A  G  R  I  I  T  E  S  L  N  T  S  Q  Y  T  Y  E  I
        370       380       390       400       410       420       430       440       450       460       470       480
gccctgtgttgtcctcatggaagaggaggtgctgaagaaactccgtgccctggtgggctgaactctggggatgggtcttctgtcctggtggctccatctcgaacatgtatgccatg
 A  P  V  F  V  L  M  E  E  V  L  K  K  L  R  A  L  V  G  W  N  S  G  D  V  F  C  P  G  G  S  I  S  N  M  Y  A  M
        490       500       510       520       530       540       550       560       570       580       590       600
aacctggcccgctatcagcgctaccccagactgcaagcaaagaggcctccgggccctgccgcccttggctctcttcacttcaaaggagtgtcactactccatcagtaagggagctgctttt
 N  L  A  R  Y  Q  R  Y  P  D  C  K  Q  R  G  L  R  A  L  P  P  L  A  L  F  T  S  K  E  C  H  Y  S  I  S  K  G  A  A  F
        610       620       630       640       650       660       670       680       690       700       710       720
ctgggacttggcactgacagtgtccgagtggtccaggctgatgagagaggaaatgatccctgaggatctggagaggcagatcagtctggctgaggcagagggctctgtgccatttctg
 L  G  L  G  T  D  S  V  R  V  V  K  A  D  E  R  G  K  M  I  P  E  D  L  E  R  Q  I  S  L  A  E  A  E  G  S  V  P  F  L
        730       740       750       760       770       780       790       800       810       820       830       840
gtcagtaccacctctggtaccacccgtgctagggcctttgaccccctggatgcaattgctgatgtttgccagcgtcacggattatggttacacgtggatgccgcctggggtgggagcgtc
 V  S  T  T  S  G  T  T  V  L  G  A  F  D  P  L  D  A  I  A  D  V  C  Q  R  H  G  L  W  L  H  V  D  A  A  W  G  G  S  V
        850       860       870       880       890       900       910       920       930       940       950       960
ctgctgtcccggacacacaggcatctcctggatgggatccagagggctgactctgtggcctggaaccctcacaagctctcggtgcagggctgcagtgctctgctcttcttctccgggac
 L  L  S  R  T  H  R  H  L  L  D  G  I  Q  R  A  D  S  V  A  W  N  P  H  K  L  L  G  A  G  L  Q  C  S  A  L  L  L  R  D
        970       980       990      1000      1010      1020      1030      1040      1050      1060      1070      1080
acctcgaacctgctcaagcgctgccatgggtccaggccagctacctgttccagcaggacaaattctatgacgtggctcttgacactggagacaaggtggtgcagtgtggccgccgtgtg
 T  S  N  L  L  K  R  C  H  G  S  Q  A  S  Y  L  F  Q  Q  D  K  F  Y  D  V  A  L  D  T  G  D  K  V  V  Q  C  G  R  R  V
       1090      1100      1110      1120      1130      1140      1150      1160      1170      1180      1190      1200
gactgtctgaagttgtggctcatgtggaaggcacagggtgggcaaggactggagcggcgcatcgaccaggcctttgctctcacccggtacctggtggaggagataaaaaagcgggaagga
 D  C  L  K  L  W  L  M  W  K  A  Q  G  G  Q  G  L  E  R  R  I  D  Q  A  F  A  L  T  R  Y  L  V  E  E  I  K  K  R  E  G
       1210      1220      1230      1240      1250      1260      1270      1280      1290      1300      1310      1320
tttgagttggtcatggagcctgagtttgtcaatgtgtgcttctggtttgtgcctcccagcctgcgggggaagaaagagagtccagattacagcaaaggctgtctcaggtggcgcctgta
 F  E  L  V  M  E  P  E  F  V  N  V  C  F  W  F  V  P  P  S  L  R  G  K  K  E  S  P  D  Y  S  K  R  L  S  Q  V  A  P  V
       1330      1340      1350      1360      1370      1380      1390      1400      1410      1420      1430      1440
ctcaaggagcgcatggtgaagaagggctccatgatgattggctaccagccccatgggacccgggccaacttcttccggatggtggtggccaacccacactgacccaggctgatatagac
 L  K  E  R  M  V  K  K  G  S  M  M  I  G  Y  Q  P  H  G  T  R  A  N  F  F  R  M  V  V  A  N  P  T  L  T  Q  A  D  I  D
       1450      1460      1470      1480
ttcctctgggcgagctggagcgtctgggccaggacctgtga
 F  L  L  G  E  L  E  R  L  G  Q  D  L  *
```

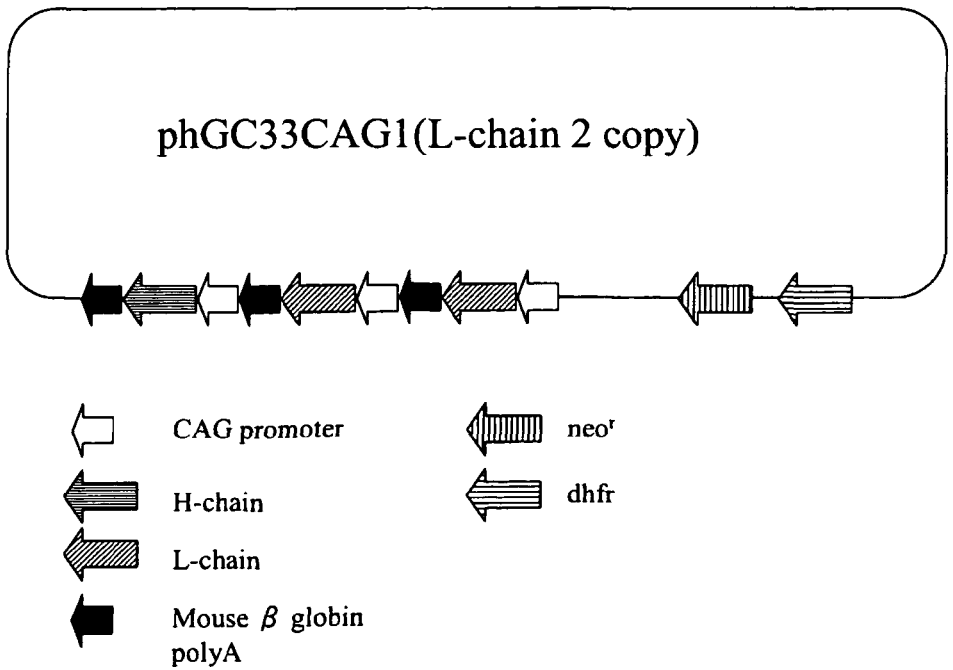

Fig. 10

SEQUENCE LISTING

```
<160> NUMBER OF SEQ ID NOS: 8

<210> SEQ ID NO 1
<211> LENGTH: 1869
<212> TYPE: DNA
<213> ORGANISM: Cricetulus griseus
<220> FEATURE:
<221> NAME/KEY: CDS
<222> LOCATION: (1)..(1866)

<400> SEQUENCE: 1 atg gcc acc aag gag aag ctg cag tgt ctg aaa gac ttc cac aaa gac      48
Met Ala Thr Lys Glu Lys Leu Gln Cys Leu Lys Asp Phe His Lys Asp
1               5                   10                  15 atc ctg aag cct tct cca ggg aag agc cca ggc aca cgg cct gag gat      96
Ile Leu Lys Pro Ser Pro Gly Lys Ser Pro Gly Thr Arg Pro Glu Asp
            20                  25                  30 gag gct gag ggg aag ccc cct cag agg gag aag tgg tcc agc aag att      144
Glu Ala Glu Gly Lys Pro Pro Gln Arg Glu Lys Trp Ser Ser Lys Ile
        35                  40                  45 gac ttt gtg ctg tct gtg gcc gga ggc ttc gtg ggt ttg ggc aac gtt      192
Asp Phe Val Leu Ser Val Ala Gly Gly Phe Val Gly Leu Gly Asn Val
    50                  55                  60 tgg cgt ttc ccg tac ctc tgc tac aaa aat ggt gga ggt gct ttc ctc      240
Trp Arg Phe Pro Tyr Leu Cys Tyr Lys Asn Gly Gly Gly Ala Phe Leu
65                  70                  75                  80 ata ccg tat ttt att ttc ctg ttt ggg agt ggc ctg cct gtg ttt ttc      288
```

```
                    Ile Pro Tyr Phe Ile Phe Leu Phe Gly Ser Gly Leu Pro Val Phe Phe
                                    85                  90                  95 ctg gag gtc ata ata ggc cag tac acc tca gaa ggg gga atc acc tgc        336
Leu Glu Val Ile Ile Gly Gln Tyr Thr Ser Glu Gly Gly Ile Thr Cys
            100                 105                 110 tgg gag aag atc tgc ccc ttg ttc tct ggc att ggc tac gca tcc atc        384
Trp Glu Lys Ile Cys Pro Leu Phe Ser Gly Ile Gly Tyr Ala Ser Ile
            115                 120                 125 gtc atc gtg tcc ctc ctg aat gtg tac tac att gtc atc ctg gcc tgg        432
Val Ile Val Ser Leu Leu Asn Val Tyr Tyr Ile Val Ile Leu Ala Trp
            130                 135                 140 gcc aca tac tac cta ttt cac tcc ttc cag aca gag ctt ccc tgg gcc        480
Ala Thr Tyr Tyr Leu Phe His Ser Phe Gln Thr Glu Leu Pro Trp Ala
145                 150                 155                 160 cac tgc aac cac agc tgg aac aca cca cat tgc atg gag gac acc ctg        528
His Cys Asn His Ser Trp Asn Thr Pro His Cys Met Glu Asp Thr Leu
                165                 170                 175 cgt agg aat gag agt ctc tgg gtc tcc ctt agc gcc tcc aac ttc acc        576
Arg Arg Asn Glu Ser Leu Trp Val Ser Leu Ser Ala Ser Asn Phe Thr
                180                 185                 190 tcg cct gtc atc gag ttc tgg gag cgc aat gta ctc agc ctg tct tcc        624
Ser Pro Val Ile Glu Phe Trp Glu Arg Asn Val Leu Ser Leu Ser Ser
                195                 200                 205 gga atc gac gaa cca ggc gct ctg aaa tgg gac ctt gcg ctc tgc ctc        672
Gly Ile Asp Glu Pro Gly Ala Leu Lys Trp Asp Leu Ala Leu Cys Leu
210                 215                 220 ctc tta gtc tgg ctt gtc tgt ttt ttc tgc ata tgg aag ggt gtt cga        720
Leu Leu Val Trp Leu Val Cys Phe Phe Cys Ile Trp Lys Gly Val Arg
225                 230                 235                 240 tcc aca ggc aag gtt gtc tac ttc acc gcc act ttc ccg ttt gcc atg        768
Ser Thr Gly Lys Val Val Tyr Phe Thr Ala Thr Phe Pro Phe Ala Met
                245                 250                 255 ctt ctg gtg ctg ctg gtc cgt gga ctg acc ctg ccg ggt gct ggc gaa        816
Leu Leu Val Leu Leu Val Arg Gly Leu Thr Leu Pro Gly Ala Gly Glu
                260                 265                 270 ggc atc aaa ttc tac ctg tac cct gac atc agc cgc ctt gag gac cca        864
Gly Ile Lys Phe Tyr Leu Tyr Pro Asp Ile Ser Arg Leu Glu Asp Pro
                275                 280                 285 cag gtg tgg atc gac gcc gga acc cag ata ttc ttt tcc tat gcc atc        912
Gln Val Trp Ile Asp Ala Gly Thr Gln Ile Phe Phe Ser Tyr Ala Ile
            290                 295                 300 tgc ctg ggg gcc atg acc tca ctg gga agc tac aac aag tac aag tat        960
Cys Leu Gly Ala Met Thr Ser Leu Gly Ser Tyr Asn Lys Tyr Lys Tyr
305                 310                 315                 320 aac tcg tac agg gac tgt atg ctg ctg gga tgc ctg aac agt ggt acc       1008
Asn Ser Tyr Arg Asp Cys Met Leu Leu Gly Cys Leu Asn Ser Gly Thr
                325                 330                 335 agt ttt gtg tct ggc ttc gca gtt ttt tcc atc ctg ggc ttc atg gca       1056
Ser Phe Val Ser Gly Phe Ala Val Phe Ser Ile Leu Gly Phe Met Ala
                340                 345                 350 caa gag caa ggg gtg gac att gct gat gtg gct gag tca ggt cct ggc       1104
Gln Glu Gln Gly Val Asp Ile Ala Asp Val Ala Glu Ser Gly Pro Gly
                355                 360                 365 ttg gcc ttc att gcc tat cca aaa gct gtg act atg atg ccg ctg ccc       1152
Leu Ala Phe Ile Ala Tyr Pro Lys Ala Val Thr Met Met Pro Leu Pro
                370                 375                 380 acc ttt tgg tcc att ctg ttt ttt att atg ctc ctc ttg ctt gga ctg       1200
Thr Phe Trp Ser Ile Leu Phe Phe Ile Met Leu Leu Leu Leu Gly Leu
385                 390                 395                 400
```

```
gac agc cag ttt gtt gaa gtc gaa gga cag atc aca tcc ttg gtt gat    1248
Asp Ser Gln Phe Val Glu Val Glu Gly Gln Ile Thr Ser Leu Val Asp
            405                 410                 415 ctt tac ccg tcc ttc cta agg aag ggt tat cgt cgg gaa gtc ttc atc    1296
Leu Tyr Pro Ser Phe Leu Arg Lys Gly Tyr Arg Arg Glu Val Phe Ile
            420                 425                 430 gcc atc ctg tgt agc atc agc tac ctg ctg ggg ctg tcg atg gtg acg    1344
Ala Ile Leu Cys Ser Ile Ser Tyr Leu Leu Gly Leu Ser Met Val Thr
            435                 440                 445 gag ggt ggc atg tat gtg ttt caa ctc ttt gac tac tat gca gct agt    1392
Glu Gly Gly Met Tyr Val Phe Gln Leu Phe Asp Tyr Tyr Ala Ala Ser
            450                 455                 460 ggt gta tgc ctt ttg tgg gtt gca ttc ttt gaa tgt ttt gtt att gcc    1440
Val Cys Leu Leu Trp Val Ala Phe Phe Glu Cys Phe Val Ile Ala
465                 470                 475                 480 tgg ata tat ggt ggt gat aac tta tat gac ggt att gag gac atg att    1488
Trp Ile Tyr Gly Gly Asp Asn Leu Tyr Asp Gly Ile Glu Asp Met Ile
            485                 490                 495 ggc tat cgg cct ggg ccc tgg atg aag tac agc tgg gct gtc atc act    1536
Gly Tyr Arg Pro Gly Pro Trp Met Lys Tyr Ser Trp Ala Val Ile Thr
            500                 505                 510 cca gtt ctc tgt gct gga tgt ttc atc ttc tct ctt gtc aag tat gta    1584
Pro Val Leu Cys Ala Gly Cys Phe Ile Phe Ser Leu Val Lys Tyr Val
            515                 520                 525 ccc ctg acc tac aac aaa gtc tac gtg tat cct gat tgg gca att ggg    1632
Pro Leu Thr Tyr Asn Lys Val Tyr Val Tyr Pro Asp Trp Ala Ile Gly
            530                 535                 540 ctg ggc tgg ggc ctg gcc cta tcc tcc atg gtg tgt atc ccc ttg gtc    1680
Leu Gly Trp Gly Leu Ala Leu Ser Ser Met Val Cys Ile Pro Leu Val
545                 550                 555                 560 att gcc atc ctc ctc tgc cgg acg gag gga ccg ttc cgc gtg aga atc    1728
Ile Ala Ile Leu Leu Cys Arg Thr Glu Gly Pro Phe Arg Val Arg Ile
            565                 570                 575 caa tac ctg ata acc ccc agg gag ccc aac cgc tgg gct gtg gag cgt    1776
Gln Tyr Leu Ile Thr Pro Arg Glu Pro Asn Arg Trp Ala Val Glu Arg
            580                 585                 590 gag ggg gcc aca ccc ttc cac tcc cgc aca agc ctc gtc atg aac ggc    1824
Glu Gly Ala Thr Pro Phe His Ser Arg Thr Ser Leu Val Met Asn Gly
            595                 600                 605 gca ctc atg aaa ccc agt cac gtc att gtg gag acc atg atg tga        1869
Ala Leu Met Lys Pro Ser His Val Ile Val Glu Thr Met Met
            610                 615                 620

<210> SEQ ID NO 2
<211> LENGTH: 622
<212> TYPE: PRT
<213> ORGANISM: Cricetulus griseus

<400> SEQUENCE: 2

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80
```

-continued

```
Ile Pro Tyr Phe Ile Phe Leu Phe Gly Ser Gly Leu Pro Val Phe Phe
             85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
            115                 120                 125

Val Ile Val Ser Leu Leu Asn Val Tyr Tyr Ile Val Ile Leu Ala Trp
            130                 135                 140

Ala Thr Tyr Tyr Leu Phe His Ser Phe Gln Thr Glu Leu Pro Trp Ala
145                 150                 155                 160

His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
            180                 185                 190

Ser Pro Val Ile Glu Phe Trp Glu Arg Asn Val Leu Ser Leu Ser Ser
            195                 200                 205

Gly Ile Asp Glu Pro Gly Ala Leu Lys Trp Asp Leu Ala Leu Cys Leu
            210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Glu Asp Pro
            275                 280                 285

Gln Val Trp Ile Asp Ala Gly Thr Gln Ile Phe Phe Ser Tyr Ala Ile
            290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Val Phe Ser Ile Leu Gly Phe Met Ala
            340                 345                 350

Gln Glu Gln Gly Val Asp Ile Ala Asp Val Ala Glu Ser Gly Pro Gly
            355                 360                 365

Leu Ala Phe Ile Ala Tyr Pro Lys Ala Val Thr Met Met Pro Leu Pro
            370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
            405                 410                 415

Leu Tyr Pro Ser Phe Leu Arg Lys Gly Tyr Arg Arg Glu Val Phe Ile
            420                 425                 430

Ala Ile Leu Cys Ser Ile Ser Tyr Leu Leu Gly Leu Ser Met Val Thr
            435                 440                 445

Glu Gly Gly Met Tyr Val Phe Gln Leu Phe Asp Tyr Tyr Ala Ala Ser
            450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
```

```
                500                 505                 510
Pro Val Leu Cys Ala Gly Cys Phe Ile Phe Ser Leu Val Lys Tyr Val
            515                 520                 525

Pro Leu Thr Tyr Asn Lys Val Tyr Val Tyr Pro Asp Trp Ala Ile Gly
            530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575

Gln Tyr Leu Ile Thr Pro Arg Glu Pro Asn Arg Trp Ala Val Glu Arg
            580                 585                 590

Glu Gly Ala Thr Pro Phe His Ser Arg Thr Ser Leu Val Met Asn Gly
            595                 600                 605

Ala Leu Met Lys Pro Ser His Val Ile Val Glu Thr Met Met
            610                 615                 620

<210> SEQ ID NO 3
<211> LENGTH: 1482
<212> TYPE: DNA
<213> ORGANISM: Cricetulus griseus
<220> FEATURE:
<221> NAME/KEY: CDS
<222> LOCATION: (1)..(1479)

<400> SEQUENCE: 3 atg gct gac tca aaa cca ctc aat gcc ctg gat ggg gac cct gtg gct      48
Met Ala Asp Ser Lys Pro Leu Asn Ala Leu Asp Gly Asp Pro Val Ala
1               5                   10                  15 gtg gag tcc tta ctc cgg gat gtg ttt ggg att gtt gta gat gag gcc      96
Val Glu Ser Leu Leu Arg Asp Val Phe Gly Ile Val Val Asp Glu Ala
                20                  25                  30 att cgg aaa ggg acc agt gcc tcg gag aag gtt tgt gaa tgg aag gag     144
Ile Arg Lys Gly Thr Ser Ala Ser Glu Lys Val Cys Glu Trp Lys Glu
            35                  40                  45 cct gaa gag ctc aag cat ctg ctg gat ttg gag ctg cag agc cag ggc     192
Pro Glu Glu Leu Lys His Leu Leu Asp Leu Glu Leu Gln Ser Gln Gly
        50                  55                  60 gag tct caa gag cag att cta gag cgc tgc cgg gct gtg att cac tac     240
Glu Ser Gln Glu Gln Ile Leu Glu Arg Cys Arg Ala Val Ile His Tyr
65                  70                  75                  80 agt gtc aag act ggt cac ccc cgg ttc ttc aac cag ctc ttc tca ggg     288
Ser Val Lys Thr Gly His Pro Arg Phe Phe Asn Gln Leu Phe Ser Gly
                85                  90                  95 tta gac ccc cat gct ctg gct ggg cgc atc atc aca gaa agc ctc aac     336
Leu Asp Pro His Ala Leu Ala Gly Arg Ile Ile Thr Glu Ser Leu Asn
                100                 105                 110 acc agc cag tac aca tat gag att gcc cct gtg ttt gtc ctc atg gaa     384
Thr Ser Gln Tyr Thr Tyr Glu Ile Ala Pro Val Phe Val Leu Met Glu
            115                 120                 125 gag gag gtg ctg aag aaa ctc cgt gcc ctg gtg ggc tgg aac tct ggg     432
Glu Glu Val Leu Lys Lys Leu Arg Ala Leu Val Gly Trp Asn Ser Gly
        130                 135                 140 gat ggg gtc ttc tgt cct ggt ggc tcc atc tcg aac atg tat gcc atg     480
Asp Gly Val Phe Cys Pro Gly Gly Ser Ile Ser Asn Met Tyr Ala Met
145                 150                 155                 160 aac ctg gcc cgc tat cag cgc tac cca gac tgc aag caa aga ggc ctc     528
Asn Leu Ala Arg Tyr Gln Arg Tyr Pro Asp Cys Lys Gln Arg Gly Leu
                165                 170                 175 cgg gcc ctg ccg ccc ttg gct ctc ttc act tca aag gag tgt cac tac     576
```

```
                Arg Ala Leu Pro Pro Leu Ala Leu Phe Thr Ser Lys Glu Cys His Tyr
                            180                 185                 190 tcc atc agt aag gga gct gct ttt ctg gga ctt ggc act gac agt gtc        624
Ser Ile Ser Lys Gly Ala Ala Phe Leu Gly Leu Gly Thr Asp Ser Val
            195                 200                 205 cga gtg gtc aag gct gat gag aga ggg aaa atg atc cct gag gat ctg        672
Arg Val Val Lys Ala Asp Glu Arg Gly Lys Met Ile Pro Glu Asp Leu
    210                 215                 220 gag agg cag atc agt ctg gct gag gca gag ggc tct gtg cca ttt ctg        720
Glu Arg Gln Ile Ser Leu Ala Glu Ala Glu Gly Ser Val Pro Phe Leu
225                 230                 235                 240 gtc agt acc acc tct ggt acc acc gtg cta ggg gcc ttt gac ccc ctg        768
Val Ser Thr Thr Ser Gly Thr Thr Val Leu Gly Ala Phe Asp Pro Leu
                245                 250                 255 gat gca att gct gat gtt tgc cag cgt cac gga tta tgg tta cac gtg        816
Asp Ala Ile Ala Asp Val Cys Gln Arg His Gly Leu Trp Leu His Val
            260                 265                 270 gat gcc gcc tgg ggt ggg agc gtc ctg ctg tcc cgg aca cac agg cat        864
Asp Ala Ala Trp Gly Gly Ser Val Leu Leu Ser Arg Thr His Arg His
        275                 280                 285 ctc ctg gat ggg atc cag agg gct gac tct gtg gcc tgg aac cct cac        912
Leu Leu Asp Gly Ile Gln Arg Ala Asp Ser Val Ala Trp Asn Pro His
    290                 295                 300 aag ctt ctc ggt gca ggg ctg cag tgc tct gct ctt ctc ctc cgg gac        960
Lys Leu Leu Gly Ala Gly Leu Gln Cys Ser Ala Leu Leu Leu Arg Asp
305                 310                 315                 320 acc tcg aac ctg ctc aag cgc tgc cat ggg tcc cag gcc agc tac ctg       1008
Thr Ser Asn Leu Leu Lys Arg Cys His Gly Ser Gln Ala Ser Tyr Leu
                325                 330                 335 ttc cag cag gac aaa ttc tat gac gtg gct ctt gac act gga gac aag       1056
Phe Gln Gln Asp Lys Phe Tyr Asp Val Ala Leu Asp Thr Gly Asp Lys
            340                 345                 350 gtg gtg cag tgt ggc cgc cgt gtg gac tgt ctg aag ttg tgg ctc atg       1104
Val Val Gln Cys Gly Arg Arg Val Asp Cys Leu Lys Leu Trp Leu Met
        355                 360                 365 tgg aag gca cag ggt ggg caa gga ctg gag cgg cgc atc gac cag gcc       1152
Trp Lys Ala Gln Gly Gly Gln Gly Leu Glu Arg Arg Ile Asp Gln Ala
    370                 375                 380 ttt gct ctc acc cgg tac ctg gtg gag gag ata aaa aag cgg gaa gga       1200
Phe Ala Leu Thr Arg Tyr Leu Val Glu Glu Ile Lys Lys Arg Glu Gly
385                 390                 395                 400 ttt gag ttg gtc atg gag cct gag ttt gtc aat gtg tgc ttc tgg ttt       1248
Phe Glu Leu Val Met Glu Pro Glu Phe Val Asn Val Cys Phe Trp Phe
                405                 410                 415 gtg cct ccc agc ctg cgg ggg aag aaa gag agt cca gat tac agc aaa       1296
Val Pro Pro Ser Leu Arg Gly Lys Lys Glu Ser Pro Asp Tyr Ser Lys
            420                 425                 430 agg ctg tct cag gtg gcg cct gta ctc aag gag cgc atg gtg aag aag       1344
Arg Leu Ser Gln Val Ala Pro Val Leu Lys Glu Arg Met Val Lys Lys
        435                 440                 445 ggc tcc atg atg att ggc tac cag ccc cat ggg acc cgg gcc aac ttc       1392
Gly Ser Met Met Ile Gly Tyr Gln Pro His Gly Thr Arg Ala Asn Phe
    450                 455                 460 ttc cgg atg gtg gtg gcc aac ccc aca ctg acc cag gct gat ata gac       1440
Phe Arg Met Val Val Ala Asn Pro Thr Leu Thr Gln Ala Asp Ile Asp
465                 470                 475                 480 ttc ctt ctg ggc gag ctg gag cgt ctg ggc cag gac ctg tga              1482
Phe Leu Leu Gly Glu Leu Glu Arg Leu Gly Gln Asp Leu
                485                 490
```

<210> SEQ ID NO 4
<211> LENGTH: 493
<212> TYPE: PRT
<213> ORGANISM: Cricetulus griseus

<400> SEQUENCE: 4

```
Met Ala Asp Ser Lys Pro Leu Asn Ala Leu Asp Gly Asp Pro Val Ala
1               5                   10                  15

Val Glu Ser Leu Leu Arg Asp Val Phe Gly Ile Val Val Asp Glu Ala
                20                  25                  30

Ile Arg Lys Gly Thr Ser Ala Ser Glu Lys Val Cys Glu Trp Lys Glu
            35                  40                  45

Pro Glu Glu Leu Lys His Leu Leu Asp Leu Glu Leu Gln Ser Gln Gly
        50                  55                  60

Glu Ser Gln Glu Gln Ile Leu Glu Arg Cys Arg Ala Val Ile His Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Asn Ser Gly
130                 135                 140

Asp Gly Val Phe Cys Pro Gly Gly Ser Ile Ser Asn Met Tyr Ala Met
145                 150                 155                 160

Asn Leu Ala Arg Tyr Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Ser Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
210                 215                 220

Glu Arg Gln Ile Ser Leu Ala Glu Ala Glu Gly Ser Val Pro Phe Leu
225                 230                 235                 240

Val Ser Thr Thr Ser Gly Thr Thr Val Leu Gly Ala Phe Asp Pro Leu
                245                 250                 255

Asp Ala Ile Ala Asp Val Cys Gln Arg His Gly Leu Trp Leu His Val
            260                 265                 270

Asp Ala Ala Trp Gly Gly Ser Val Leu Leu Ser Arg Thr His Arg His
        275                 280                 285

Leu Leu Asp Gly Ile Gln Arg Ala Asp Ser Val Ala Trp Asn Pro His
        290                 295                 300

Lys Leu Leu Gly Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Arg Arg Ile Asp Gln Ala
        370                 375                 380
```

```
Phe Ala Leu Thr Arg Tyr Leu Val Glu Glu Ile Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Lys Glu Ser Pro Asp Tyr Ser Lys
            420                 425                 430

Arg Leu Ser Gln Val Ala Pro Val Leu Lys Glu Arg Met Val Lys Lys
        435                 440                 445

Gly Ser Met Met Ile Gly Tyr Gln Pro His Gly Thr Arg Ala Asn Phe
    450                 455                 460

Phe Arg Met Val Val Ala Asn Pro Thr Leu Thr Gln Ala Asp Ile Asp
465                 470                 475                 480

Phe Leu Leu Gly Glu Leu Glu Arg Leu Gly Gln Asp Leu
                485                 490

<210> SEQ ID NO 5
<211> LENGTH: 10
<212> TYPE: RNA
<213> ORGANISM: Artificial Sequence
<220> FEATURE:
<223> OTHER INFORMATION: Description of Artificial Sequence: Synthetic
      kozak sequence

<400> SEQUENCE: 5 gccrccaugg                                                                10

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      secretion signal sequence

<400> SEQUENCE: 6

Met Gly Trp Ser Cys Ile Ile Leu Phe Leu Val Ala Thr Ala Thr Gly
1               5                   10                  15

Val His Ser

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 cagggggccag tggatagacc gatg                                                24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctcactgga tggtgggaag atg                                                 23
```

METHOD FOR PRODUCING A CELL FOR PROTEIN PRODUCTION BY TREATING A CELL OVEREXPRESSING A TAURINE TRANSPORTER WITH METHOTREXATE

CROSS-REFERENCE TO RELATED APPLICATIONS

This application is a National Stage application of PCT/JP2008/068589, filed Oct. 14, 2008, which claims priority from Japanese application JP 2007-267384, filed Oct. 15, 2007.

TECHNICAL FIELD

The present invention relates to a method for producing a cell capable of high-yield production of heteroproteins.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

It has been known that the number of copies of dihydrofolate reductase (DHFR) gene is amplified (gene amplification) in cells by methotrexate (MTX), whereby the cells become MTX-resistant. Widely used in industrial production is a method for increasing the amount of useful protein production, in which plasmids having a gene of the protein connected downstream of the DHFR gene are introduced into animal cells which are then cultured in an MTX-supplemented medium to induce gene amplification (Patent Document 1).

[Patent Document 1]
Japanese Patent Publication No. 6-30588

DISCLOSURE OF THE INVENTION

Problem for Solution by the Invention

An object of the present invention is to provide a cell capable of high-yield production of proteins and a method for producing the same.

Means to Solve the Problem

The present inventors devoted their full effort to solve the aforementioned problem. As a result, they found that host cells acquired MTX-resistance by strongly expressing a taurine transporter (TauT) in the cells, and cells that had come to produce an antibody following introduction of a gene of the antibody thereinto acquired MTX-resistance by strongly expressing TauT in the cells, and further, an antibody production ability of antibody-producing cells in which TauT and cysteine sulfinic acid decarboxylase (CSAD) were co-expressed was improved by treating the cells with a high concentration of MTX; these findings led to completion of the present invention.

The present invention is summarized as follows.

(1) A method for producing a cell capable of high-yield production of a desired polypeptide, wherein a strongly taurine transporter-expressing cell into which DNA encoding the desired polypeptide has been introduced is cultured in the presence of a high concentration of methotrexate and a cell capable of high-yield production of the desired polypeptide is selected from among surviving cells.

(2) The method according to (1) above, wherein DNA encoding dihydrofolate reductase (DHFR) is also introduced into the strongly taurine transporter-expressing cell into which DNA encoding the desired polypeptide has been introduced.

(3) The method according to (2) above, wherein the strongly taurine transporter-expressing cell into which DNA encoding the desired polypeptide has been introduced is a cell that is co-transformed with one molecule containing DNA encoding the desired polypeptide and DNA encoding dihydrofolate reductase (DHFR).

(4) The method according to (3) above, wherein the molecule containing DNA encoding the desired polypeptide and DNA encoding dihydrofolate reductase (DHFR) is a vector.

(5) The method according to any one of (1) to (4) above, wherein the strongly taurine transporter-expressing cell also strongly expresses cysteine sulfinic acid decarboxylase.

(6) A cell produced by a method according to any one of (1) to (5) above.

(7) A method for producing a desired polypeptide, wherein the cell according to (6) above is cultured.

(8) The method according to (7) above, wherein the desired polypeptide is an antibody.

(9) A method for producing a pharmaceutical product containing a polypeptide produced by the method according to (7) or (8).

(10) A method for enhancing the amount of polypeptide production by a strongly taurine transporter-expressing cell into which DNA encoding a desired polypeptide has been introduced, the method comprising treating the cell is treated with a high concentration of methotrexate.

(11) The method according to (10) above, wherein DNA encoding dihydrofolate reductase is also introduced into the strongly taurine transporter-expressing cell into which DNA encoding the desired polypeptide has been introduced.

(12) The method according to (11) above, wherein the strongly taurine transporter-expressing cell into which DNA encoding the desired polypeptide has been introduced is a cell that is co-transformed with one molecule containing DNA encoding the desired polypeptide and DNA encoding dihydrofolate reductase.

(13) The method according to any one of (10) to (12) above, wherein the strongly taurine transporter-expressing cell also strongly expresses cysteine sulfinic acid decarboxylase.

(14) A method for producing a cell capable of high-yield production of a desired polypeptide, wherein a strongly taurine transporter-expressing cell into which DNA encoding the desired polypeptide has been introduced is cultured in the presence of methotrexate and a cell capable of high-yield production of the desired polypeptide is selected from among surviving cells.

(15) A method for enhancing the amount of polypeptide produced by a strongly taurine transporter-expressing cell into which DNA encoding a desired polypeptide has been introduced, the method comprising treating the cell with methotrexate.

EFFECT OF THE INVENTION

The present invention enabled high-yield production of desired polypeptides including an antibody.

The present specification encompasses the contents disclosed in the specification and/or the drawings of Japanese Patent Application No. 2007-267384 based on which the present patent application claims priority.

BRIEF DESCRIPTION OF THE DRAWINGS

FIG. 7 shows the nucleotide sequence (SEQ ID NO: 1) of a newly cloned, CHO cell-derived hamster taurine transporter gene and the amino acid sequence (SEQ ID NO: 2) deduced therefrom.

FIG. 9 shows the nucleotide sequence (SEQ ID NO: 3) of a newly cloned, CHO cell-derived hamster CSAD gene and the amino acid sequence (SEQ ID NO: 4) deduced therefrom.

FIG. 10 shows phGC33CAG1, which is an expression plasmid for a humanized anti-human glypican-3 antibody.

BEST MODE FOR CARRYING OUT THE INVENTION

Figure 1:
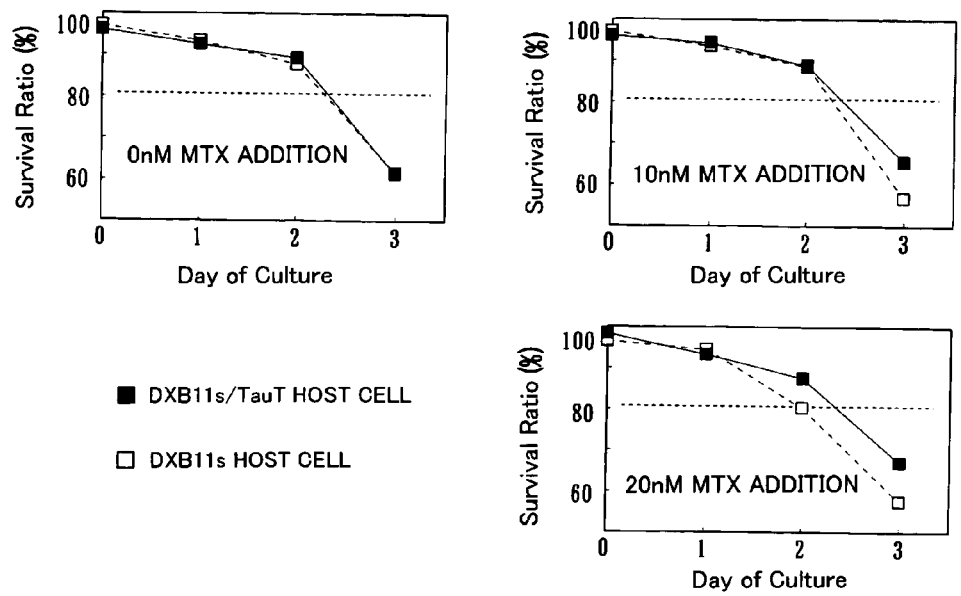
FIG. 1 shows host cells in which TauT is strongly expressed take on MTX-resistance.

Hereinbelow, embodiments of the present invention will be described in more detail.

The present invention provides a method for producing a cell capable of high-yield production of a desired polypeptide, wherein a strongly TauT expressing cell into which DNA encoding the desired polypeptide has been introduced is cultured in the presence of a high concentration of MTX and a cell capable of high-yield production of the desired polypeptide is selected from among surviving cells.

According to the method of the present invention, a strongly TauT expressing cell into which DNA encoding the desired polypeptide has been introduced is cultured in the presence of a high concentration of MTX.

DNA encoding the desired polypeptide is introduced into a strongly TauT expressing cell.

In the method of the present invention, the desired polypeptide is not particularly limited. The polypeptide may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

It is known that taurine transporter is a membrane protein having the function of taking up amino acids (such as taurine and β-alanine) into cells.

A cell which strongly expresses a taurine transporter is not particularly limited as long as the cell has an increased expression level of a taurine transporter compared to a corresponding natural cell. The natural cell is not particularly limited. A cell which is used as a host in the production of a recombinant protein (e.g., CHO cells) may be used.

While a strongly TauT expressing cell can be any cell that may be eukaryotic cells including an animal cell, a plant cell, and yeast; or prokaryotic cells including *Escherichia coli* and *Bacillus subtilis*, a cultured cell employed as a host in the production of a recombinant protein is appropriate. Animal cells such as a CHO cell and a COS cell are preferable, among which a CHO cell is particularly preferable. Also, in order to produce a desired polypeptide, a dhfr-deficient CHO cell (for example, a DXB 11 cell line of CHO cells or a DG44 cell line of CHO cells) is particularly preferable. Because a dhfr-deficient CHO cell is auxotrophic for hypoxanthine and thymidine, the cell cannot grow in a medium deprived of hypoxanthine and thymidine (hereinafter expressed as "medium without HT"); however, the cell becomes able to grow in the medium without HT once it is transformed with a recombinant vector containing a DHFR gene. Accordingly, it is convenient to use a dhfr-deficient CHO cell as a host because a transformed cell can be selected by utilizing the auxotrophy of the cell for hypoxanthine and thymidine.

As a cell which strongly expresses a taurine transporter, a cell into which a taurine transporter gene has been artificially transferred may be given. A cell into which a taurine transporter gene has been artificially transferred can be prepared by methods known to those skilled in the art. For example, such a cell may be prepared by incorporating a taurine transporter gene into a vector and transforming the vector into a cell. Furthermore, the concept of "cells into which a TauT gene has been artificially transferred" encompasses herein cells in which an endogenous TauT gene has been activated by gene activation technology (see, for example, International Publication WO94/12650) so that TauT is strongly expressed.

As TauT to be strongly expressed in a cell, TauT derived from any organism may be used. Specifically, TauT derived from human or a rodent (such as mouse, rat or hamster) may be used. Preferably, TauT derived from human, a rodent or the same species as the host cell may be used. For example, when the cell which is allowed to strongly express TauT is a Chinese hamster ovary cell (CHO cell), TauT is preferably derived from human or hamster.

Further, as a TauT gene to be strongly expressed in a cell, any one of the following DNAs (a) to (e) encoding TauT may be used.

(a) a DNA encoding a polypeptide having the amino acid sequence as shown in SEQ ID NO: 2 or the amino acid sequence of SC6A6_RAT (P31643), SC6A6_MOUSE (O35316), SC6A6_HUMAN (P31641), SC6A6_BOVIN (Q9MZ34) or SC6A6_CANFA (Q00589) in UniProt Knowledgebase;

(b) a DNA encoding a polypeptide which has an amino acid sequence derived from the amino acid sequence as shown in SEQ ID NO: 2 or the amino acid sequence of SC6A6_RAT (P31643), SC6A6_MOUSE (035316), SC6A6_HUMAN (P31641), SC6A6_BOVIN (Q9MZ34) or SC6A6_CANFA (Q00589) in UniProt Knowledgebase by substitution, deletion, addition and/or insertion of one or more amino acid residues and yet has TauT activity;

(c) a DNA encoding a polypeptide having 70% or more amino acid sequence homology with the amino acid sequence as shown in SEQ ID NO: 2 or the amino acid sequence of SC6A6_RAT (P31643), SC6A6_MOUSE (O35316), SC6A6_HUMAN (P31641), SC6A6_BOVIN (Q9MZ34) or SC6A6_CANFA (Q00589) in UniProt Knowledgebase and yet having TauT activity;

(d) a DNA having the nucleotide sequence as shown in SEQ ID NO: 1 or the nucleotide sequence of M96601, L03292, Z18956, AF260239 or M95495 in GenBank;

(e) a DNA which hybridizes to a DNA complementary to a DNA having the nucleotide sequence as shown in SEQ ID NO: 1 or the nucleotide sequence of M96601, L03292, Z18956, AF260239 or M95495 in GenBank under stringent conditions and yet encodes a polypeptide having TauT activity.

The DNA of (a) is a DNA encoding hamster, rat, mouse, human, cattle or dog TauT, as exemplified as the DNA of (d).

The DNA of (b) is a DNA encoding a polypeptide functionally equivalent to hamster, rat, mouse, human, cattle or dog TauT, as exemplified by a polypeptide having an amino acid sequence derived from the amino acid sequence of the hamster, rat, mouse, human, cattle or dog TauT by deletion of one or more amino acids, preferably 1-30 amino acids, more preferably 1-10 amino acids; a polypeptide having an amino acid sequence derived from the amino acid sequence of the hamster, rat, mouse, human, cattle or dog TauT by addition of one or more amino acids, preferably 1-30 amino acids, more preferably 1-10 amino acids; and a polypeptide having an amino acid sequence derived from the amino acid sequence of the hamster, rat, mouse, human, cattle or dog TauT by substitution of one or more amino acids, preferably 1-30 amino acids, more preferably 1-10 amino acids, with other amino acids.

The expression "functionally equivalent to hamster, rat, mouse, human, cattle or dog TauT" means having activities similar to the activities of hamster, rat, mouse, human, cattle or dog TauT, such as taurine-binding activity, activity to transport taurine into cells, etc. Such a polypeptide encompasses, for example, mutants of hamster, rat, mouse, human, cattle or dog TauT. It also encompasses TauT derived from other biological species.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, H, K, S and T), amino acids with an aliphatic side chain (G; A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

The DNA of (c) encodes a polypeptide functionally equivalent to hamster, rat, mouse, human, cattle or dog TauT, which is a polypeptide having at least 70% (preferably 97% or more homology, more preferably 98% or more homology, even more preferably 99% or more homology with the amino acid sequence of the hamster, rat, mouse, human, cattle or dog TauT. For determination of the homology of polypeptides, the algorithm described in Wilbur, W. J. and Lipman, D. J., Proc. Natl. Acad. Sci. USA (1983) 80, 726-730 may be followed.

The DNA may be prepared by methods known to those skilled in the art. For example, the DNA may be prepared by preparing a cDNA library from a cell expressing hamster, rat, mouse, human, cattle or dog TauT and performing hybridization using a part of the DNA sequence of the hamster, rat, mouse, human, cattle or dog TauT (e.g., SEQ ID NO: 1) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA of hamster, rat, mouse, human, cattle or dog TauT by preparing RNA from a cell expressing the hamster, rat, mouse, human, cattle or dog TauT, synthesizing oligo DNA molecules based on the DNA sequence of the hamster, rat, mouse, human, cattle or dog TauT (e.g., SEQ ID NO: 1), and performing PCR using the oligo DNA molecules as primers to thereby amplify a cDNA encoding the TauT.

Further, by determining the nucleotide sequence of the resultant cDNA, it is possible to determine the translation region encoding the polypeptide and to obtain the amino acid sequence of hamster, rat, mouse, human, cattle or dog TauT or a polypeptide functionally equivalent thereto. Further, by screening a genomic library using the resultant cDNA as a probe, it is possible to isolate a genomic DNA.

Specifically, the following procedures may be used. First, mRNA is isolated from cells, tissues or the like expressing hamster, rat, mouse, human, cattle or dog TauT. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with primers. Further, point mutagenesis may be used to introduce a mutation into DNA thus obtained. DNA thus mutated can then be amplified by PCR.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA by considering the frequency of codon usage in the host to be used for expression (Grantham, R. et al., Nucleic Acids Research (1981) 9, p. 43-74). Further, the DNA can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA of (e) is a DNA which hybridizes to a DNA complementary to a DNA having the nucleotide sequence as shown in SEQ ID NO: 1 or the nucleotide sequence of M96601, L03292, Z18956, AF260239 or M95495 in GenBank under stringent conditions and encodes a polypeptide functionally equivalent to hamster, rat, mouse, human, cattle or dog TauT. Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA. These DNAs isolated by hybridization techniques usually have a high nucleotide sequence identity with the nucleotide sequence as shown in SEQ ID NO: 1 or the nucleotide sequence of M96601, L03292, Z18956, AF260239 or M95495 in GenBank. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score =100 and word-length =12, for example. Specific procedures for these analysis methods are known (ncbi.nlm.nih.gov.).

When a cell into which a TauT gene has been artificially transferred is used, the order of the transfer of a TauT gene and the transfer of a DNA encoding a desired polypeptide is not particularly limited. A DNA encoding a desired polypeptide may be transferred after the transfer of a TauT gene. Alternatively, a TauT gene may be transferred after the transfer of a DNA encoding a desired polypeptide. It is also possible to transfer a TauT gene and a DNA encoding a desired polypeptide simultaneously.

A cell strongly expressing TauT may also strongly express CSAD.

As a cell which strongly expresses CSAD, a cell into which a CSAD gene has been artificially transferred may be given. A cell into which a CSAD gene has been artificially transferred can be prepared by methods known to those skilled in the art. For example, such a cell may be prepared by incorporating a CSAD gene into a vector and transforming the vector into a cell. Furthermore, the concept of "cells into which a CSAD gene has been artificially transferred" encompasses herein cells in which an endogenous CSAD gene has been activated by gene activation technology (see, for example, International Publication WO94/12650) so that CSAD is strongly expressed.

As CSAD to be strongly expressed in a cell, CSAD derived from any organism may be used. Specifically, CSAD derived from human, a rodent (such as mouse, rat or hamster), a puffer (such as Tiger puffer) or a sea squirt (such as *Ciona intestnalis*) may be used. Preferably, CSAD derived from human, a rodent or the same species as the host cell may be used. For example, when the cell which is allowed to strongly express CSAD is a Chinese hamster ovary cell (CHO cell), the CSAD is preferably derived from human or hamster.

Further, as a CSAD gene to be strongly expressed in a cell, any one of the following DNAs (a1) to (e1) may be used.

(a1) a DNA encoding a polypeptide having the amino acid sequence as shown in SEQ ID NO: 4 or the amino acid sequence of CSAD_RAT (Q64611), CSAD_MOUSE (Q9 DBE0) or CSAD_HUMAN (Q9Y600) in UniProt Knowledgebase;

(b1) a DNA encoding a polypeptide which has an amino acid sequence derived from the amino acid sequence as shown in SEQ ID NO: 4 or the amino acid sequence of CSAD_RAT (Q64611), CSAD_MOUSE (Q9 DBE0) or CSAD_HUMAN (Q9Y600) in UniProt Knowledgebase by substitution, deletion, addition and/or insertion of one or more amino acid residues and yet has CSAD activity;

(c1) a DNA encoding a polypeptide having 70% or more amino acid sequence homology with the amino acid sequence as shown in SEQ ID NO: 4 or the amino acid sequence of CSAD_RAT (Q64611), CSAD_MOUSE (Q9 DBE0) or CSAD_HUMAN (Q9Y600) in UniProt Knowledgebase and yet having CSAD activity;

(d1) a DNA having the nucleotide sequence as shown in SEQ ID NO: 3 or the nucleotide sequence of M64755, AK005015 or AF116546 in GenBank;

(e1) a DNA which hybridizes to a DNA complementary to a DNA having the nucleotide sequence as shown in SEQ ID NO: 3 or the nucleotide sequence of M64755, AK005015 or AF116546 in GenBank under stringent conditions and yet encodes a polypeptide having CSAD activity.

DNA of (a1) is DNA encoding hamster, rat, mouse, or human CSAD. For an example, it may be DNA of (d1). An enzyme activity of cattle CSAD is identified; however, no information is available for the sequence thereof.

The DNA of (b1) is a DNA encoding a polypeptide functionally equivalent to hamster, rat, mouse or human CSAD, as exemplified by a polypeptide having an amino acid sequence derived from the amino acid sequence of the hamster, rat, mouse or human CSAD by deletion of one or more amino acids, preferably 1-30 amino acids, more preferably 1-10 amino acids; a polypeptide having an amino acid sequence derived from the amino acid sequence of the hamster, rat, mouse or human CSAD by addition of one or more amino acids, preferably 1-30 amino acids, more preferably 1-10 amino acids; and a polypeptide having an amino acid sequence derived from the amino acid sequence of the hamster, rat, mouse or human CSAD by substitution of one or more amino acids, preferably 1-30 amino acids, more preferably 1-10 amino acids, with other amino acids.

The expression "a polypeptide that is functionally equivalent to hamster, rat, mouse or human CSAD" is used to mean that the polypeptide has a decarboxylation activity that is equivalent to the activity possessed by hamster, rat, mouse or human CSAD, such as enzyme activity for synthesizing hypotaurine from 3-sulfinic acid alanine, enzyme activity for synthesizing taurine from cysteic acid, and enzyme activity as of glutamate decarboxylase for synthesizing β-alanine from aspartic acid. Such a polypeptide encompasses, for example, mutants of hamster, rat, mouse or human CSAD. It also encompasses CSAD derived from other biological species (e.g., cattle CSAD and the like).

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, H, K, S and T), amino acids with an aliphatic side chain (Q A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

The DNA of (c1) encodes a polypeptide functionally equivalent to hamster, rat, mouse or human CSAD, which is a polypeptide having at least 70% (preferably 97% or more homology, more preferably 98% or more homology, even more preferably 99% or more homology with the amino acid sequence of the hamster, rat, mouse or human CSAD. For determination of the homology of polypeptides, the algorithm described in Wilbur, W. J. and Lipman, D. J., Proc. Natl. Acad. Sci. USA (1983) 80, 726-730 may be followed.

The DNA may be prepared by methods known to those skilled in the art. For example, the DNA may be prepared by preparing a cDNA library from a cell expressing hamster, rat, mouse or human CSAD and performing hybridization using a part of the DNA sequence of the hamster, rat, mouse or human CSAD (e.g., SEQ ID NO: 3) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA of hamster, rat, mouse or human CSAD by preparing RNA from a cell expressing the hamster, rat, mouse or human CSAD, synthesizing oligo DNA molecules based on the DNA sequence of the hamster, rat, mouse, human, cattle or dog TauT (e.g., SEQ ID NO: 3), and performing PCR using the oligo DNA molecules as primers to thereby amplify a cDNA encoding the CSAD.

Further, by determining the nucleotide sequence of the resultant cDNA, it is possible to determine the translation region encoding the polypeptide and to obtain the amino acid sequence of hamster, rat, mouse or human CSAD or a polypeptide functionally equivalent thereto. Further, by screening a genomic library using the resultant cDNA as a probe, it is possible to isolate a genomic DNA.

Specifically, the following procedures may be used. First, mRNA is isolated from cells, tissues or the like expressing hamster, rat, mouse or human CSAD. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Beyavsky, A. et al., Nucleic Acids Res. (1989) 17, 2919-2932) using 5'-Ampli FINDER RACE Kit (Clontech) and polymerase chain reaction (PCR) with primers. Further, point mutagenesis may be used to introduce a mutation into DNA thus obtained. DNA thus mutated can then be amplified by PCR.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA by considering the frequency of codon usage in the host to be used for expression (Grantham, R. et al., Nucleic Acids Research (1981) 9, p. 43-74). Further, the DNA can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA of (e1) is a DNA which hybridizes to a DNA complementary to a DNA having the nucleotide sequence as shown in SEQ ID NO: 3 or the nucleotide sequence of M647559, AK005015 or AF116546 in GenBank under stringent conditions and encodes a polypeptide functionally equivalent to the hamster, rat, mouse or human CSAD. Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA. These DNAs isolated by hybridization techniques usually have a high nucleotide sequence identity with the nucleotide sequence as shown in SEQ ID NO: 3 or the nucleotide sequence of M64755, AK005015 or AF116546 in GenBank. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score =100 and wordlength =12, for example. Specific procedures for these analysis methods are known (ncbi.nlm.nih.gov.).

A DHFR gene may be introduced into a strongly TauT expressing cell together with DNA encoding the desired polypeptide. The number of copies of DHFR gene is amplified (gene amplification) in cells by MTX, whereby the cells take on MTX-resistant. The strongly TauT expressing cell may be obtained by co-transformation with one molecule (for example, a vector) containing DNA encoding the desired polypeptide and DNA encoding DHFR. When a recombinant vector in which DNA encoding the desired polypeptide is connected to a DHFR gene is introduced into cells and the cells thus obtained are cultured in a medium in the presence of MTX, cells capable of high-yield production of the desired polypeptide by gene amplification can be obtained. The DHFR gene may be derived from any various organisms, and their DNA sequences are publicly known (mouse: GenBank V00734, rat: GenBank AF318150, and human: GenBank J00140). Hence, the DHFR gene may be prepared in accordance with such available information and introduced into a vector. Further, a commercially available expression vector in which the DHFR gene is introduced (pOptiVEC™-TOPO (registered trademark) vector, a product of Invitrogen Corporation) can also be used.

When a cell into which a TauT gene is artificially introduced is employed as a host, DNA encoding the desired polypeptide and DNA encoding DHFR may be introduced into the cell after the TauT gene is introduced, or, in the other way around, the TauT gene may be introduced into the cell after DNA encoding the desired polypeptide and DNA encoding DHFR are introduced. Alternatively, the TauT gene, DNA encoding the desired polypeptide, and DNA encoding DHFR may be simultaneously introduced into the cell.

The TauT gene (and also the CSAD gene, in some cases) and DNA encoding the desired polypeptide may be simultaneously introduced by a single vector, or each independently introduced by using a plurality of vectors.

Furthermore, DNA encoding the desired polypeptide and the DHFR gene may be introduced into a single vector or different vectors. In order to efficiently establish a strain capable of high-yield production by gene amplification, it is preferable to introduce DNA encoding the desired polypeptide and the DHFR gene into a single vector. In order to increase an amplification efficiency of the gene, it is preferable to connect the DHFR gene downstream of a promoter having a low transcription efficiency (for example, a SV40 promoter), and connect DNA encoding the desired polypeptide downstream of a promoter having a high transcription efficiency (for example, a CMV promoter, a SRα promoter, or an EF-1α a promoter). When DNA encoding the desired polypeptide and the DHFR gene are introduced into different vectors, the vectors may be introduced into a host cell by co-transfection. In this case, the vector into which DNA encoding the desired polypeptide is incorporated is preferably introduced into the host cell in an excess amount (normally, approximately twice to 40 times in excess) over the vector into which the DHFR gene is incorporated.

For construction of a polypeptide expression vector in CHO cells, utilization of a CMV immediate-early enhancer/promoter region, a typical Kozak sequence (−6 GCCR (R=A/G) CCAUGG+4) (SEQ ID NO: 5), and a drug-resistance marker (such as neomycin, hygromycin, or puromycin), as well as addition of a secretion signal peptide (such as MGWSCIILFLVATATGVHS (SEQ ID NO: 6)) to the N-terminal side may be considered.

The expression vector may be cleaved with an appropriate restriction enzyme into a linear form before it is introduced into host cells. An expression unit of a gene of interest can be easily incorporated into the chromosome in the host cells by preparing the vector into a linear form. A gene transfer method is not particularly limited, and it may be any method such as a calcium phosphate method, a DEAE dextran method, a lipofection method, or an electroporation method. Multiple copies can be introduced by carrying out gene transfer with NUCLEOFECTOR (a product of Amaxa Biosystems).

After carrying out gene transfer into host cells, the cells are cultured in a selection medium, whereby cells into which a gene of interest has been introduced may be selected. For example, when DNA encoding the desired polypeptide is inserted in a vector having a drug-resistance gene, and host cells are transformed with the vector thus obtained and then are cultured in the medium containing a drug, surviving cells can be selected as transformed cells. Furthermore, when DNA encoding the desired polypeptide is inserted in a vector having a DHFR gene, and dhfr-deficient CHO cells, which serve as host cells, are transformed with the vector thus obtained and then cultured in a medium without HT, surviving cells can be selected as transformed cells. For the medium, a CHO-S-SFMII/CD-CHO mixed medium (a product of Invitrogen Corporation) and the like may be used. The transformed cells are continuously cultured and the amount of polypeptide of interest produced is measured after an appropriate time has passed (normally, approximately on the $14^{th}$ to $21^{st}$ day). Subsequently, cells capable of high-yield production are subjected to MTX treatment. The transformed cells to be subjected to MTX treatment are preferably capable of not only high-yield polypeptide production but also rapid proliferation. Proliferation rates can be compared by measuring the number of viable cells that have been subcultured.

The MTX treatment refers to, for example, culturing cells (preferably subculturing) in a medium to which a high concentration of MTX has been added. The high concentration refers to a concentration at least twice the normal concentration of MTX at which cell selection is performed (which is approximately 20 nM for CHO cells); for example, it is a concentration at which 90% or more of a strain into which TauT has not been introduced dies three weeks after subculturing. While the concentration varies depending on cells, in a case of CHO cells such as CHO DXB 11 s cells used in the production of a recombinant protein, a concentration of 50 nM or more is normally appropriate; it is preferably 80 nM or more, and more preferably 100 nM or more. Seven to 35 days are appropriate as a culture period; it is preferably 14 to 28 days, and more preferably 21 to 28 days.

When transformed cells are cultured in a medium to which a high concentration of MTX has been added, the concentration of MTX may be increased in a stepwise fashion. For example, the cells are cultured in a medium containing MTX at a concentration of 10 nM for 14 to 21 days, and then cultured in a medium containing MTX at a concentration of 100 nM for 14 to 28 days.

A strain capable of high-yield production may be selected in every step of culturing with the concentration of MTX being changed. Also, when cell proliferation is no longer observed due to culturing in the medium to which a high concentration of MTX has been added, cell proliferation may be recovered by putting cells back to a medium to which a low concentration of MTX has been added and then continuing culturing in that medium.

For the medium to which a high concentration of MTX is added, a CHO-S-SFMII/CD-CHO mixed medium (a product of Invitrogen Corporation) and the like can be used.

Even when a transformed strain is nearly uniform before it is subjected to MTX treatment, it will lose uniformity after MTX treatment because it will acquire diversity through the treatment. The total amount of polypeptide produced by a group of ununiform cells becomes greater than the amount produced by the nearly uniform strain before MTX treatment. It is possible to clone only a strain capable of high-yield production from a group of cells that have acquired diversity. For example, limiting dilution employing a 96-well plate and single cell cloning accomplished by a cell sorter are effective. A publicly known method can be employed for either of these methods.

The strongly TauT expressing cell of the present invention has an excellent MTX-resistant ability as revealed by the Examples described later, and therefore, the cell can be selected at a higher concentration of MTX than the normal concentration at which selection is performed.

From the group of cells of the present invention obtained through treatment with a high concentration of MTX as described above, a strain capable high-yield production of the desired polypeptide that is impossible or very difficult to obtain by normal MTX treatment can be obtained efficiently in a large number. Hence, the strongly TauT expressing cell of the present invention is extremely useful as a transformed cell to be used for MTX selection.

Accordingly, the present invention also provides a cell capable of high-yield production of the desired polypeptide that is produced by the methods described above. The cell can be a group of nonuniform cells or a cloned uniform strain.

The present invention provides a method for producing a polypeptide, wherein the cell produced by the methods described above is cultured. Furthermore, a desired polypeptide can be prepared by using a cell in which an endogenous gene has been activated by gene activation technology (see, for example, International Publication WO94/12650) so that a desired polypeptide has been produced.

For culturing the cell, media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 µg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogen-phosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

The pH of the medium varies depending on the cell to be cultured. Generally, pH 6.8-7.6 is appropriate. In many cases, pH 7.0-7.4 is appropriate.

It is also possible to use a commercial medium for animal cell culture, e.g., D-MEM (Dulbecco's Modified Eagle Medium), D-MEM/F-12 1:1 Mixture (Dulbecco's Modified Eagle Medium Nutrient Mixture F-12), RPMI1640, CHO- S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium.

When the cell is a CHO cell, the CHO cell may be cultured by methods known to those skilled in the art. For example, the CHO cell may be cultured usually in an atmosphere with a $CO_2$ concentration in the gas phase of 0 to 40%, preferably 2 to 10%, at 30 to 39° C., preferably about 37° C.

As is clear from the Examples described later, production of waste products (such as lactate) which turn to be cell growth inhibitory substances can be inhibited in a cell strongly expressing TauT. As a result, the cell shows the effect of maintaining a high survival ratio. The cell is capable of culturing for three months or a still longer period.

Further, when a desired polypeptide, such as an antibody, is produced in cultured cells, the cells come into a highly concentrated state (about $1 \times 10^7$ cells/ml) at the late-stage of culture, and the influence of waste products such as lactate becomes extremely high. When a desired polypeptide is produced using the cell strongly expressing TauT, a high survival ratio is maintained even at the late-stage of culture, and an improvement can be expected in the yield of the desired polypeptide.

An appropriate culture period for producing a desired polypeptide using the cell is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the cell is cultured, taurine may be added to the medium in order to promote taurine uptake into cells. The concentration of taurine added to the medium is not particularly limited. The concentration is usually 0-100 g/L, preferably 0-20 g/L, more preferably 0-10 g/L.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody (e.g., in the case of anticancer agent) is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc.), transnasal administration, transpulmonary administration, transdermal administration and the like may be enumerated.

In another embodiment of the present invention, there is provided a method for enhancing the amount of polypeptide production by the strongly TauT expressing cell into which DNA encoding the desired polypeptide has been introduced, the method comprising treating the cell with a high concentration of MTX.

In the present invention, the concept of "cells into which DNA has been transferred" encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Preparation Example 1

Production of an Expression Plasmid for a Humanized Anti-Human Glypican-3 Antibody An H chain gene of a humanized anti-human glypican-3 antibody was prepared as follows. A mouse (MRL/1 pr, a product of Charles River Laboratories Japan, Inc.) was immunized with glypican-3 fragments (which were obtained by expressing a gene of a GST-fusion protein obtained by PCR). A hybridoma was then prepared using spleen cells obtained from the mouse. The hybridoma was screened by ELISA using glypican-3 as an antibody, whereby a clone capable of producing a glypican-3-binding antibody was selected. Then, mRNA was extracted from the hybridoma, and cDNA was prepared therefrom by a reverse transcription reaction using reverse transcriptase. An H chain variable region gene of a mouse anti-glypican-3 antibody was amplified by PCR using a primer (CAGGGGCCAGTGGATA-GACCGATG) (SEQ ID NO: 7), which had cDNA and a base sequence complementary to a mouse H chain variable region gene, and the gene was obtained by binding to pGEM-T Easy (a product of Promega Corporation). An H chain variable region gene of a human antibody that had a homology with a framework region of the H chain variable region gene of a mouse anti-glypican-3 antibody was identified by searching through the Kabat database. A base sequence of an H chain variable region gene of a humanized anti-glypican-3 antibody, in which each framework part of the H chain variable region gene of a human antibody thus identified was connected to each CDR part of the H chain variable region gene of a mouse anti-glypican-3 antibody, was designed and then synthesized by PCR. The H chain variable region gene of a humanized anti-glypican-3 antibody was then connected to a human IgG1 constant region gene, and the H chain gene of a humanized anti-glypican-3 antibody was produced through optimization by amino acid substitution (see WO 06/06693). Then, an H chain gene of a humanized anti-human glypican-3 antibody was connected downstream of a CAG promoter, and a mouse β-globin poly(A) signal was connected further downstream thereof, whereby an H chain expression unit was produced. The H chain expression unit can be excised by BamHI and HindIII located upstream of the unit and XhoI located downstream of the same.

Then, an L chain gene of a humanized anti-human glypican-3 antibody was prepared as follows. A mouse was immunized with glypican-3 fragments. A hybridoma was then prepared using spleen cells obtained from the mouse. The hybridoma was screened by ELISA using glypican-3 as an antibody, whereby a clone capable of producing a glypican-3-binding antibody was selected. Then, mRNA was extracted from the hybridoma, and cDNA was prepared therefrom by a reverse transcription reaction using reverse transcriptase. An L chain variable region gene of a mouse anti-glypican-3 antibody was amplified by PCR using a primer (GCTCACTGGATGGTGGGAAGATG) (SEQ ID NO: 8), which had cDNA and a base sequence complementary to a mouse L chain variable region gene, and the gene was obtained by binding to pGEM-T Easy (a product of Promega Corporation). An L chain variable region gene of a human antibody that had a homology with a framework region of the L chain variable region gene of a mouse anti-glypican-3 antibody was identified by searching through the Kabat database. A base sequence of an L chain variable region gene of a humanized anti-glypican-3 antibody, in which each framework part of the L chain variable region gene of a human antibody thus identified was connected to each CDR part of the H chain variable region gene of a mouse anti-glypican-3 antibody, was designed and then synthesized by PCR. The L chain variable region gene of a humanized anti-glypican-3 antibody was then connected to a human IgG κ constant region gene, and an L chain gene of a humanized anti-glypican-3 antibody was produced through optimization by amino acid substitution (see WO 06/06693). Then, an L chain gene of a humanized anti-human glypican-3 antibody was connected downstream of a CAG promoter, and a mouse β-globin poly(A) signal was connected further downstream thereof, whereby an L chain expression unit was produced. The L chain expression unit can be excised by HindIII.

INPEP4, a plasmid produced by IDEC Corporation, was digested by BamHI and XhoI and connected to the H chain expression unit to produce pINP-CG33-H1. Then, pINP-CG33-H1 digested by HindIII and the L chain expression unit excised by HindIII were connected. By the operation described above, phGC33CAG1, an L chain 2-copy expression plasmid containing two copies of the L chain expression unit and one copy of the H chain expression unit per plasmid was produced (FIG. 10).

Example 1

Acquisition of MTX-Resistance by Introduction of Hamster Taurine Transporter (TauT)

Figure 5:
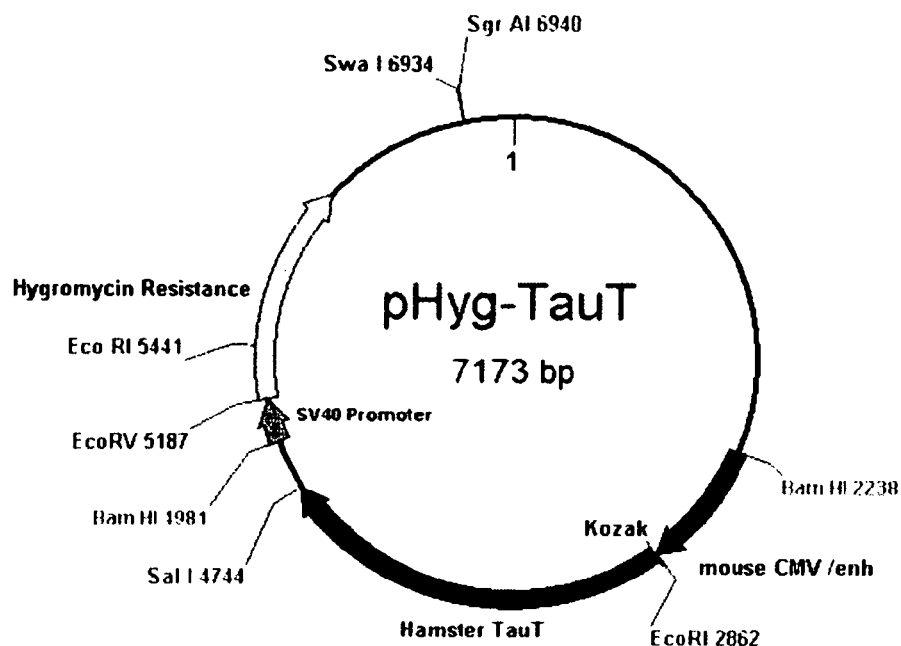
FIG. 5 shows a plasmid for hygromycin-selection, in which hamster TauT (622 amino acids) was expressed.

Into CHO DXB 11 s cells serving as host cells, pHyg-TauT expression plasmids (see Referential Example 2 described later, FIG. 5) were introduced by electroporation to prepare DXB 11 s/TauT host cells in which TauT was strongly expressed. Subsequently, sensitivity to MTX was compared between the DXB 11 s/TauT host cells and the DXB 11 s host cells which were the parent strain. Because both of the DXB 11 s/TauT host cells and the DXB 11s host cells were deficient in DHFR gene (auxotrophic for HT), their survival rates equally decreased when they were cultured in the CHO-S-SFM II/CD-CHO mixed medium without HT in the absence of MTX (FIG. 1, "0 nM MTX addition"). When 10 nM or 20 nM of MTX was added, a tendency of accelerated decrease in the survival rate was observed in the DXB 11 s host cells on account of the cytotoxicity of MTX. On the other hand, in the DXB 11 s/TauT host cells, reduction in the survival rate was suppressed at a level equivalent to the survival rate observed in the absence of MTX (FIG. 1, "10 nM, 20 nM MTX addition"). This result shows that the DXB 11 s/TauT host cells have MTX-resistance in comparison with the DXB 11 s host cells.

Figure 2:
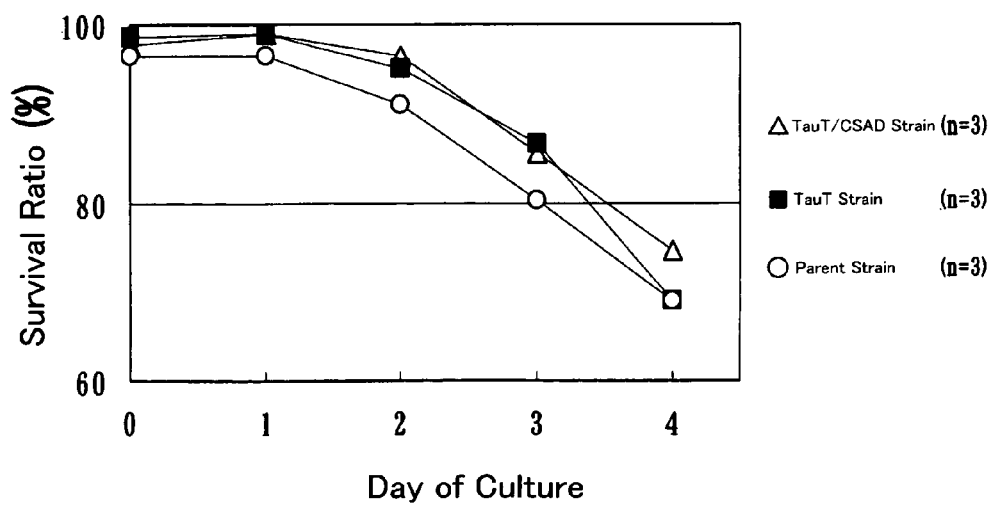
FIG. 2 shows that a TauT strain, which refers to an anti-glypican-3 antibody-producing cell in which TauT is strongly expressed, and a TauT/CSAD strain, which refers to the aforementioned antibody-producing cell in which CSAD is also strongly expressed, are more MTX-resistant than the parent strain.
Figure 6:
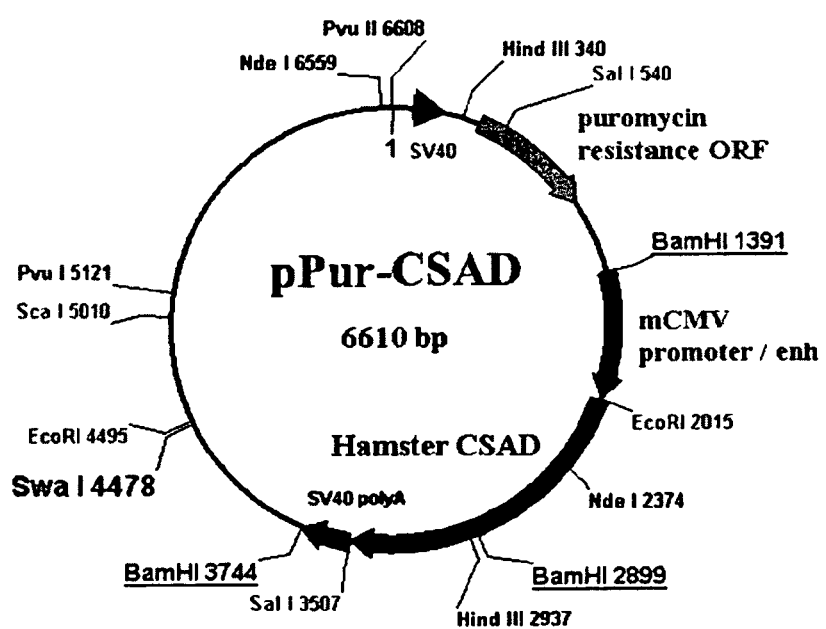
FIG. 6 shows a plasmid for puromycin-selection, in which hamster CSAD (493 amino acids) was expressed.

Then, into CHO cells capable of producing anti-glypican-3 antibody which served as the parent strain (dhfr-deficient CHO cells incorporating phGC33CAG1, the expression vector produced in Preparation Example 1, that had a CAG promoter, an anti-glypican-3 antibody gene, a mouse β-globin promoter, and a DHFR gene inserted there into), pHyg-TauT expression plasmids were introduced by electroporation to prepare a GC33/DXB11s/TauT strain in which TauT was strongly expressed. Then, pPur-CSAD expression plasmids (see Referential Example 4 described later, FIG. 6) were co-introduced into the above GC33/DXB11s/TauT strain to prepare a GC33/DXB11s/TauT/CSAD strain in which CSAD was strongly expressed. Subsequently, sensitivity to MTX of the GC33/DXB11s/TauT strain and the GC33/DXB11 s/TauT/C SAD strain was compared with that of the parent GC33/DXB11s strain. Because the parent strain was a strain capable of producing an antibody in which an antibody gene had been amplified to 20 copies or more (relative to the value before MTX treatment) by treatment with 20 nM MTX, the above strains could stably proliferate in the CHO-S-SFM II/CD-CHO mixed medium to which 20 nM MTX had been added. However, the survival rates in all of the above strains decreased on account of the cytotoxicity of MTX in the CHO-S-SFM II/CD-CHO mixed medium in which the concentration of MTX had been raised to 200 nM, which was 10 times in excess of the original concentration. This experimental system also showed that the two strains in which TauT was strongly expressed were more MTX-resistant than the parent strain (FIG. 2).

Example 2

Figure 3:
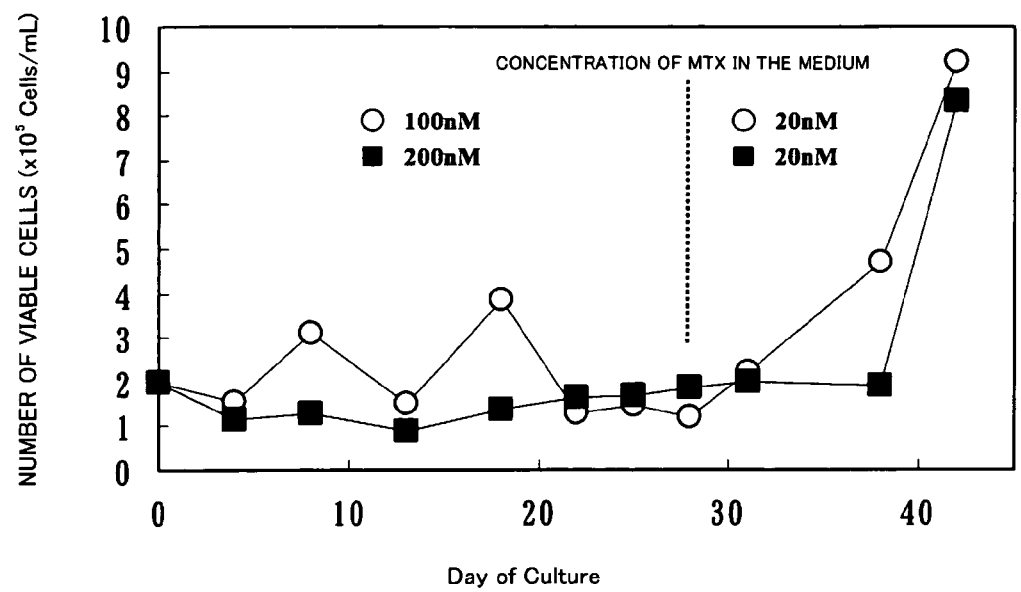
FIG. 3 shows a change in the number of cells over time when cells were continuously subcultured in the presence of a high concentration of MTX. On the 28$^{th}$ day after initiation of culture, the condition was restored to an initial condition of 20 nM MTX to recover proliferation.
Figure 4:
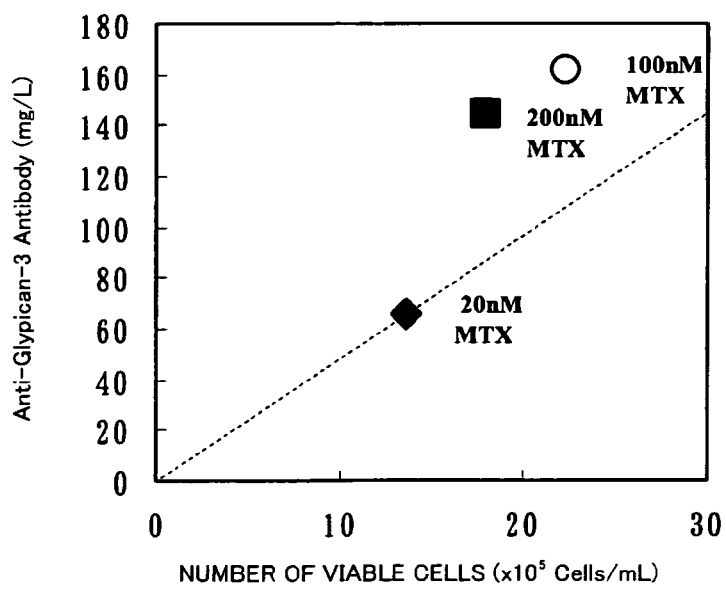
FIG. 4 shows enhanced antibody production ability of cells subsequent to treatment with a high concentration of MTX. Cells treated with 200 nM MTX exhibited the greatest amount of production per cell.

Increase in the Amount of Antibody Production by Utilization of MTX-Resistant Ability of the Strongly Taut Expressing Strain The GC33/DXB11s/TauT/CSAD strain, which was most MTX-resistant in Example 1, was subcultured in rotation culture for 28 days using the CHO-S-SFM II/CD-CHO mixed medium to which a high concentration of MTX (100 nM or 200 nM) had been added under the condition of $2\times10^5$ cells/mL in an initial stage, with the medium replaced every three to five days. As shown in FIG. 3, because no cell proliferation was observed even on the $28^{th}$ day after the initiation of the culture, the concentration of MTX was restored to the original concentration of 20 nM and then subculture was continued in rotation culture. By 14 days after that, i.e., on the $42^{nd}$ day, the cells had begun to proliferate. The above two strains in which survival rates were recovered by subculture in the diluted medium (cells treated with 100 nM or 200 nM MTX) were cultured in 15 mL tubes using the CHO-S-SFM II/CD-CHO mixed medium in the presence of 20 nM MTX under the condition of $1\times10^5$ cells/mL in an initial stage. As a result, the levels of cell proliferation of the GC33/DXB 11 s/TauT/CSAD strain before and after treatment with a high concentration of MTX were different and the strain treated with 200 nM MTX had the highest production ability (the number of viable cells: $18.0\times10^5$ cells/mL, the amount of antibody production: 144 mg/L), while the strain treated with 100 nM MTX (the number of viable cells: $22.3\times10^5$ cells/mL, the amount of antibody production: 162 mg/L) also showed a potential to produce a greater amount of antibody than the TauT/CSAD strain before treatment with a high concentration of MTX (the number of viable cells: $13.5\times10^5$ cells/mL, the amount of antibody production: 66 mg/L) (FIG. 4). Also, the amount of antibody produced by the TauT/CSAD strain before treatment with a high concentration of MTX was 86 mg/L even when the number of viable cells grew to $19.6\times10^5$ cells/mL; thus, it was shown that the TauT/CSAD strain before treatment with a high concentration of MTX had the lowest production ability.

The results obtained as above suggest that cells acquire MTX-resistance by strongly expressing a taurine transporter (TauT) in an artificial way, and cells capable of producing a greater amount of antibody can be obtained by the treatment with a high concentration of MTX when the TauT strongly expressing cells are used as host cells.

The present invention can be applied to cells capable of producing all types of desired polypeptides (preferably an antibody).

Referential Example 1

Cloning of CHO Cell-Derived Hamster Taurine Transporter Gene

Figure 7:
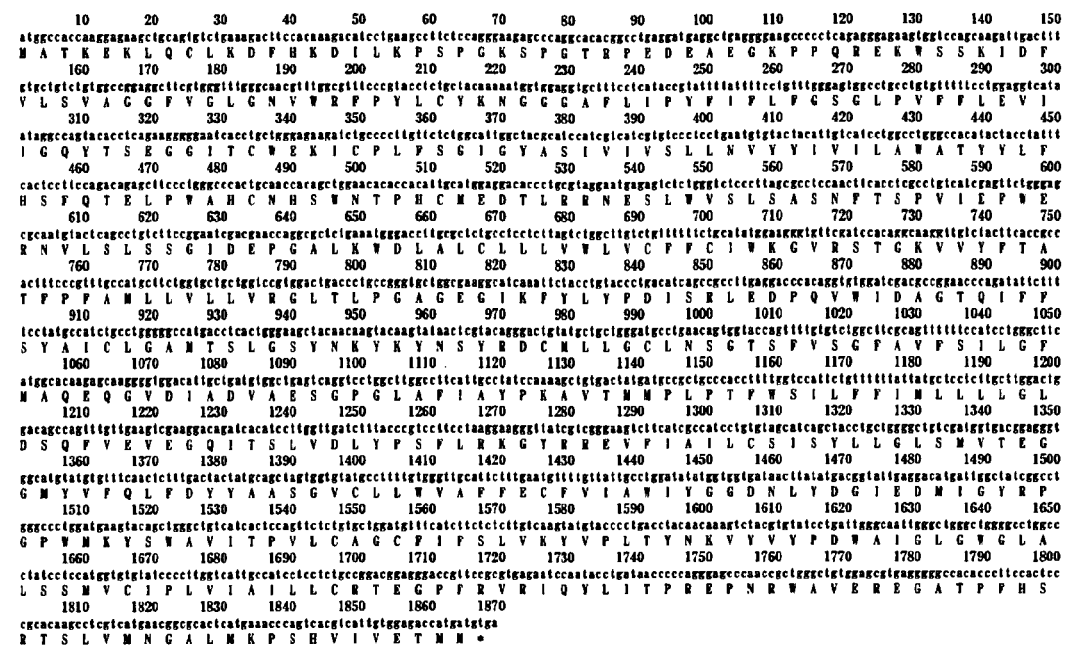
Figure 8:
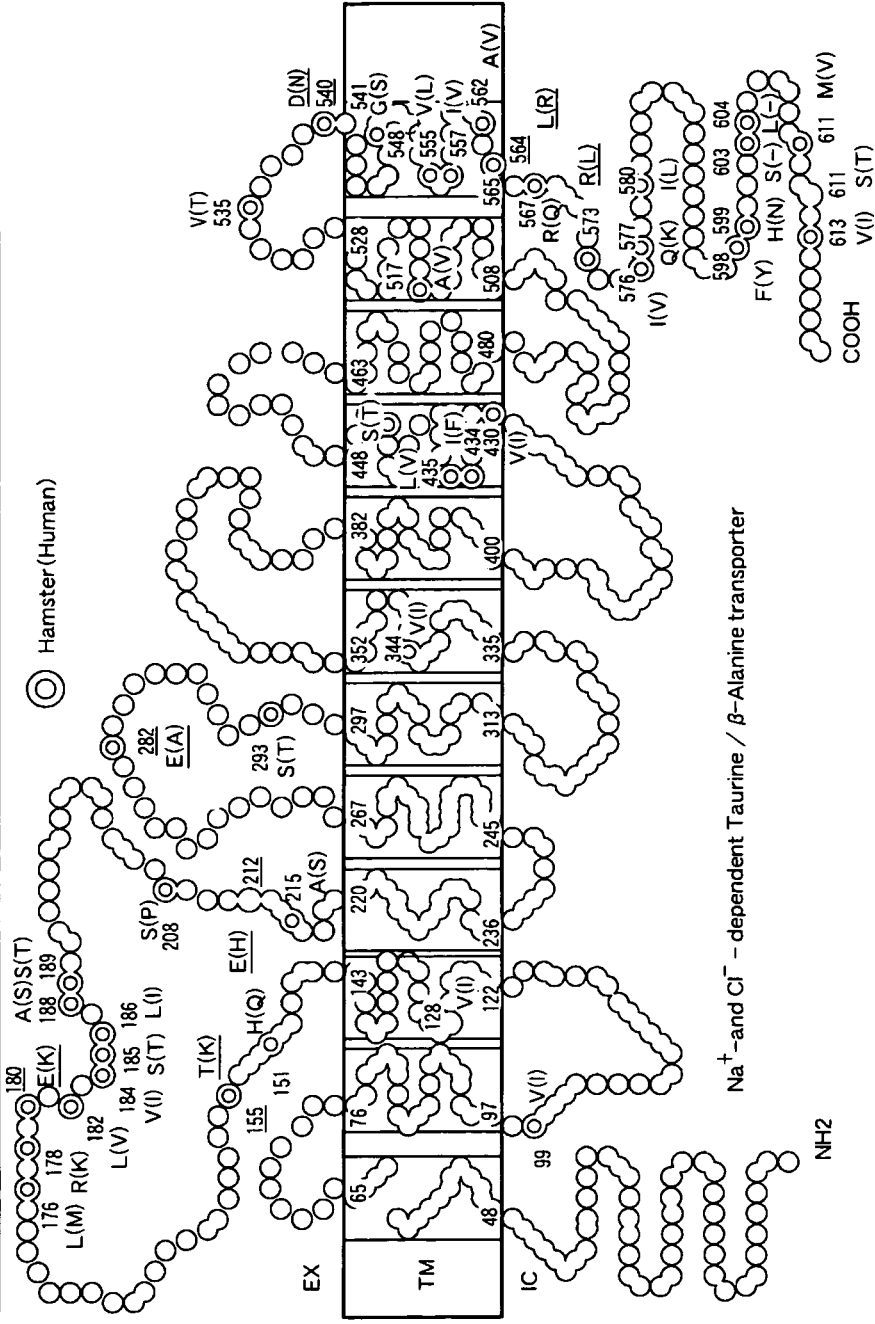
FIG. 8 is a taurine transporter membrane topology which was created based on the transmembrane regions and orientations predicted by TMpred program from the amino acid sequence of a newly cloned, CHO cell-derived hamster TauT with reference to FIG. 5 of Shinichi Uchida et al., Proc. Natl. Acad. Sci. USA Vol. 89, pp. 8230-8234, September 1992. Mark ⊚ indicates hamster TauT specific amino acid residues. A large number of amino acid residues different from those in human TauT are present in the 2nd loop (EX: extra-cell membrane region), the 12th transmembrane region (TM) and the C-terminal (IC: intracellular region).

Total RNA was extracted from anti-IL-6 receptor antibody-producing cells (A CHO DXB 11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI, XhoI and EcoRI. As PCR primers, those containing the 5'-end and the 3'-end sequence conserved between rat and mouse TauTs were designed. The nucleotide sequence of the cloned gene was determined. From its homology with other TauT genes of known species, the cloned gene was confirmed to encode hamster TauT (FIG. 7). The amino acid sequence of hamster TauT has high homology with mouse TauT (96% identity), rat TauT (96% identity) and human TauT (93% identity); it was predicted that hamster TauT is a transporter with 12 transmembrane regions (FIG. 8). The nucleotide sequence of hamster TauT is shown in SEQ ID NO: 1. The amino acid sequence of hamster TauT is shown in SEQ ID NO: 2.

Referential Example 2

Increase in Viable Cell Density, Inhibition of Lactate Production and Increase in Antibody Yield, as Caused by Transfer of Hamster Taurine Transporter CMV promoter expression plasmid pHyg/TauT (FIG. 5) was constructed by adding Kozak sequence to the hamster TauT (hereinafter, TauT) gene obtained by cloning in Referential Example 1. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 μg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2\times10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities ($9.28\pm3.27\times10^5$ cells/ml) and lactate yields ($1.54\pm0.20$ g/L) in pHyg/TauT transferred cells were superior to those in pHyg transferred cells (viable cell density: $5.69\pm2.09\times10^5$ cells/ml, lactate yield: $1.75\pm0.15$ g/L) (t test; $p<0.05$). With respect to anti-glypican-3 antibody yield, 4 out of the 7 strains of pHyg/TauT-transferred cell (mean antibody yield: 440.6 mg/L) showed antibody yields higher than the highest yield in pHyg-transferred cell (389.6 mg/L). Further, since superiority of pHyg/TauT transferred cells in anti-glypican-3 antibody yield became more evident (t test; $P<0.01$; FIG. 7) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture, with inhibited lactate production. Consequently, its anti-glypican-3 antibody yield achieved 2.9 g/L on day 35 of culture. It was confirmed by flow cytometric analysis that TauT-transferred T10 cell was expressing TauT molecules on the cell membrane. These results suggest that by artificially expressing hamster Taut, it is possible to raise the potential of antibody-producing cells and create strains capable of enhanced antibody production.

Referential Example 3

Cloning of CHO Cell-Derived Hamster Cysteine Sulfinic Acid Decarboxylase (CSAD) Gene Total RNA was extracted from anti-IL-6 receptor antibody-producing cells (A CHO DXB 11 cell line into which an anti-IL-6 receptor antibody gene had been transferred) (Japanese Unexamined Patent Publication No. Hei 8-99902), and then cDNA was synthesized therefrom in a poly(A) dependent manner. Hamster CSAD gene was obtained by PCR using as a template the cDNA fragmented with three restriction enzymes, SalI, XhoI and EcoRI. As PCR primers, those containing the 5'-end and the 3'-end sequence conserved between rat and mouse CSADs were designed. The nucleotide sequences of the cloned genes were determined. From its homology with other CSAD genes of known species, the cloned gene was confirmed to encode hamster CASD (FIG. 9). The amino acid sequence of hamster CSAD has high homology with the known amino acid sequences of mouse CSAD (96% identity), rat CSAD (96% identity) and human CSAD (91% identity); it was predicted that hamster CSAD is an enzyme having the same activity. The nucleotide sequence of hamster CSAD is shown in SEQ ID NO: 3. The amino acid sequence of hamster CSAD is shown in SEQ ID NO: 4.

Referential Example 4

Construction of a Hamster CSAD Expressing Plasmid for Puromycin-Selection

CMV promoter expression plasmid pPur/CSAD (FIG. 6) was constructed by adding Kozak sequence to the hamster CSAD (hereinafter, CSAD) gene obtained by cloning in Referential Example 3.

All publications, patent and patent applications cited herein are incorporated herein by reference in their entirety.

INDUSTRIAL APPLICABILITY

The present invention is applicable to production of proteins.

SEQUENCE LISTING FREE TEXT

<SEQ ID NO: 1>
SEQ ID NO: 1 shows the nucleotide sequence of a gene encoding hamster TauT.
<SEQ ID NO: 2>
SEQ ID NO: 2 shows the amino acid sequence of hamster TauT.
<SEQ ID NO: 3>
SEQ ID NO: 3 shows the nucleotide sequence of a gene encoding hamster CSAD.
<SEQ ID NO: 4>
SEQ ID NO: 4 shows the amino acid sequence of hamster CSAD.
<SEQ ID NO: 5>
SEQ ID NO: 5 shows a Kozak sequence.
<SEQ ID NO: 6>
SEQ ID NO: 6 shows a secretion signal peptide sequence.
<SEQ ID NO: 7>
SEQ ID NO: 7 shows a sequence of a primer having a base sequence complementary to a mouse H chain variable region gene.
<SEQ ID NO: 8>
SEQ ID NO: 8 shows a sequence of a primer having a base sequence complementary to a mouse L chain variable region gene.

---

The invention claimed is:

1. A method for producing a cell capable of increasing production of a desired antibody by expressing a taurine transporter within the cell, comprising:
   (i) preparing a taurine transporter-expressing cell transfected with
      (a) a DNA encoding a taurine transporter selected from the group consisting of a human, mouse, rat, hamster, bovine and dog taurine transporter,
      (b) a DNA encoding the desired antibody, and
      (c) a DNA encoding dihydrofolate reductase,
   (ii) subculturing the taurine transporter-expressing cell in a culture medium comprising methotrexate (MTX) at a concentration of 200 nM, wherein the medium is replaced every three to five days of the subculturing with a medium comprising MTX at a concentration of 200 nM,
   (iii) subculturing the taurine transporter-expressing cell in a culture medium comprising MTX at a concentration of 20 nM in order to proliferate the cell, wherein the subculturing of (ii) is before the subculturing of (iii); and
   (iv) selecting a cell from among surviving cells that exhibits increased production of the desired antibody and that is more MTX-resistant relative to a cell that is not transfected with the DNA encoding the taurine transporter.

2. The method according to claim 1, wherein the taurine transporter-expressing cell is co-transfected with a polynucleotide comprising both the DNA encoding the desired antibody and the DNA encoding dihydrofolate reductase.

3. The method according to claim 2, wherein the polynucleotide comprising both the DNA encoding the desired antibody and the DNA encoding dihydrofolate reductase is a vector.

4. The method according to claim 1, wherein the taurine transporter-expressing cell also is transfected with a DNA encoding cysteine sulfinic acid decarboxylase.

5. A method for enhancing the amount of antibody production by a cell, wherein the cell is transfected with (i) a DNA encoding a taurine transporter selected from the group consisting of a human, mouse, rat, hamster, bovine and dog taurine transporter, (ii) a DNA encoding a desired antibody and (iii) a DNA encoding dihydrofolate reductase, the method comprising:
   (i) subculturing the transfected cell is subcultured in a culture medium comprising MTX at a concentration of 200 nM, wherein the medium is replaced every three to five days of the subculturing with medium comprising MTX at a concentration of 200 nM; and
   (ii) subculturing the transfected cell in a culture medium comprising MTX at a concentration of 20 nM, wherein the subculturing of (i) is before the subculturing of (ii), thereby enhancing the amount of antibody production by the cell.

6. The method according to claim 5, wherein the transfected cell is co-transfected with a polynucleotide comprising both the DNA encoding the desired antibody and the DNA encoding dihydrofolate reductase.

7. The method according to claim 5, wherein the transfected cell also is transfected with a DNA encoding cysteine sulfinic acid decarboxylase.

8. A method for producing a cell capable of increasing production of a desired antibody by expressing a taurine transporter within the cell, comprising:
   (i) preparing a taurine transporter-expressing cell transfected with
      (a) a DNA encoding a taurine transporter selected from the group consisting of a human, rat, hamster, bovine and dog taurine transporter,
      (b) a DNA encoding the desired antibody, and
      (c) a DNA encoding dihydrofolate reductase,
   (ii) subculturing the taurine transporter-expressing cell in a culture medium comprising MTX at a concentration of 200 nM, wherein the medium is replaced every three to five days of the subculturing with medium comprising MTX at a concentration of 200 nM,
   (iii) subculturing the taurine transporter-expressing cell in a culture medium comprising MTX at a concentration of 20 nM in order to proliferate the cell, wherein the subculturing of (ii) is before the subculturing of (iii); and
   (iv) selecting a cell from among surviving cells that exhibits increased production of the desired antibody and that is more MTX-resistant relative to a cell that is not transfected with the DNA encoding the taurine transporter.

* * * * *